United States Patent [19]
Buechler et al.

[11] Patent Number: 6,057,098
[45] Date of Patent: May 2, 2000

[54] POLYVALENT DISPLAY LIBRARIES

[75] Inventors: Joe Buechler, San Diego; Gunars Valkirs, Escondido; Jeff Gray, Solana Beach, all of Calif.

[73] Assignee: Biosite Diagnostics, Inc., San Diego, Calif.

[21] Appl. No.: 08/832,985

[22] Filed: Apr. 4, 1997

[51] Int. Cl.[7] .............................. C12Q 1/68; G01N 33/53; C12N 15/64; C12P 21/04

[52] U.S. Cl. ................................ 435/6; 435/7.1; 435/7.8; 435/91.4; 435/471; 435/489; 435/69.1; 435/69.6; 435/320.1; 536/23.1; 536/23.4; 536/23.53

[58] Field of Search .................................. 435/69.1, 69.6, 435/320.1, 6, 91.4, 7.1, 7.8, 471, 489; 536/23.1, 23.4, 23.53

[56] References Cited

U.S. PATENT DOCUMENTS

| | | |
|---|---|---|
| 5,173,418 | 12/1992 | Molin et al. . |
| 5,427,908 | 6/1995 | Dower . |
| 5,565,332 | 10/1996 | Hoogenboom et al. . |
| 5,571,698 | 11/1996 | Ladner et al. . |
| 5,658,727 | 8/1997 | Barbas et al. ............................... 435/6 |
| 5,667,988 | 9/1997 | Barbas et al. . |
| 5,766,905 | 6/1998 | Studier et al. . |
| 5,789,208 | 8/1998 | Sharon . |

FOREIGN PATENT DOCUMENTS

| | | |
|---|---|---|
| WO 92/06204 | 4/1992 | WIPO . |
| 9426787 | 11/1994 | WIPO . |

OTHER PUBLICATIONS

Cwirla Steven E. et al., "Peptides on Phage: A Vast Library of Peptides for Identifying Ligands," *Proc. Natl. Acad. Sci.*, USA, vol. 87, Biochemistry, Aug. 1990, pp. 6378–6382.

Devlin James J. et al., "Random Peptide Libraries: A Source of Specific Protein Binding Molecules," *Science*, 1990, vol. 249, pp. 404–406.

Georgiou George et al., "Display of Heterologous Proteins on the Surface of Microorganisms: From the Screening of Combinatorial Libraries to Live Recombinant Vaccines," *Nature Biotechnology*, Jan. 1997, vol. 15, pp. 29–34.

Scott Jamie K. and Smith George P., "Searching for Peptide Ligands With An Epitope Library," *Science*, 1990, vol. 249, pp. 386–388.

Winter et al., "Making Antibodies by Phage Display Technology," *Annu. Rev. Immunol.*, 1994, vol. 12, pp. 433–455.

McCafferty et al. (1994) Applied Biochemistry and Biotechnology. 47:157–173.

*Primary Examiner*—Sheela Huff
*Assistant Examiner*—Geetha P. Bansal
*Attorney, Agent, or Firm*—Townsend and Townsend and Crew LLP

[57] ABSTRACT

The invention is directed to inter alia two related but self-sufficient improvements in conventional display methods. The first improvement provides methods of enriching conventional display libraries for members displaying more than one copy of a polypeptide prior to affinity screening of such libraries with a target of interest. These methods can achieve diverse populations in which the vast majority of members retaining full-length coding sequences encode polypeptides having specific affinity for the target. In a second aspect, the invention provides methods of subcloning nucleic acids encoding displayed polypeptides of enriched libraries from a display vector to an expression vector without the need for clonal isolation of individual members. These methods result in polyclonal libraries of antibodies and other polypeptides for use, e.g., as diagnostic or therapeutic reagents.

19 Claims, 7 Drawing Sheets

| 5' PCR HEAVY CHAIN OLIGOS FOR ANTIBODIES | |
|---|---|
| OLIGO # | 5' TO 3' SEQUENCE |
| 185 | TT ACC CCT GTG GCA AAA GCC GAG GTG CAG CTT CAG GAG TCA GG |
| 186 | TT ACC CCT GTG GCA AAA GCC CAG GTC CAG CTG CAG CAG TCT GG |
| 188 | TT ACC CCT GTG GCA AAA GCC GAA GTG CAG CTG GTG GAG TCT GG |
| 187 | TT ACC CCT GTG GCA AAA GCC GAG GTG AAG CTG GTG GAA TCT GG |
| 18 | TT ACC CCT GTG GCA AAA GCC CAG GTG CAG CTG AAG GAG TCA GG |
| 19 | TT ACC CCT GTG GCA AAA GCC CAG GTT ACG CTG AAA GAG TCT GG |
| 48 | TT ACC CCT GTG GCA AAA GCC GAG GTG AAG CTG GAT GAG ACT GG |
| 49 | TT ACC CCT GTG GCA AAA GCC GAG GTA AAG CTT CTC GAG TCT GG |
| 50 | TT ACC CCT GTG GCA AAA GCC GAA ATC AGA CTG GTG GAA TCT GG |
| 53 | TT ACC CCT GTG GCA AAA GCC GAA GTG AAG CTG GTG GAG TCT GA |
| 64 | TT ACC CCT GTG GCA AAA GCC CAG GTT CAG CTG CAA CAG TCT GA |
| 66 | TT ACC CCT GTG GCA AAA GCC GAG ATC CAG CTG CAG CAG TCT GG |
| 67 | TT ACC CCT GTG GCA AAA GCC GAA GTG ATC CTG GTG GAG TCT GG |
| 68 | TT ACC CCT GTG GCA AAA GCC GAG GTG CAG CCT GTT GAG TCT GG |
| 69 | TT ACC CCT GTG GCA AAA GCC GAC GTG AAG CAT ATG GAG TCT GG |
| 70 | TT ACC CCT GTG GCA AAA GCC GAA GTG AAG CTT GAG GAG TCT GG |
| 71 | TT ACC CCT GTG GCA AAA GCC GAG GTC CAG CTT CAG CAG TCA GG |
| 73 | TT ACC CCT GTG GCA AAA GCC CAG GTC CAG CTG CAG CAG TCT AG |
| 74 | TT ACC CCT GTG GCA AAA GCC CAG GTC CAG CTG CAG CAG TCT CG |
| 75 | TT ACC CCT GTG GCA AAA GCC GAG GTT CAG CTG CAG CAG TCT GT |
| 124 | TT ACC CCT GTG GCA AAA GCC CAG GTC CAA CTG CAG CAG CCT GG |
| 125 | TT ACC CCT GTG GCA AAA GCC GAG GTT CAG CTG CAG CAG TCT GG |
| 126 | TT ACC CCT GTG GCA AAA GCC GAG GTC CAG CTG CAA CAA TCT GG |
| 127 | TT ACC CCT GTG GCA AAA GCC CAG GTC CAC GTG AAG CAG TCT GG |
| 204 | TT ACC CCT GTG GCA AAA GCC GAT GTG CAG CTT CAG GAG TCG GG |
| 205 | TT ACC CCT GTG GCA AAA GCC CAA GTT ACT CTA AAA GAG TCT GG |
| 207 | TT ACC CCT GTG GCA AAA GCC GAA GTG CAG CTG TTG GAG ACT GG |
| 51 | TT ACC CCT GTG GCA AAA GCC CAG ATC CAG TTG GTG CAA TCT GG |
| 63 | TT ACC CCT GTG GCA AAA GCC GAT GTG AAC TTG GAA GTG TCT GG |
| 72 | TT ACC CCT GTG GCA AAA GCC CAG GCT TAT CTA CAG CAG TCT GG |
| 206 | TT ACC CCT GTG GCA AAA GCC CAG GTC CAA GTG CAG CAG CCT GG |
| 208 | TT ACC CCT GTG GCA AAA GCC GAA GTG CAG CTG GTG GAG ACT GC |
| 526 | TT ACC CCT GTG GCA AAA GCC GAC GTG CAG GTG GTG GAG TCT GG |

*FIG. 1*

| PCR KAPPA CHAIN OLIGOS FOR ANTIBODIES | |
|---|---|
| OLIGO # | 5' TO 3' SEQUENCE |
| 96 | CT GCC CAA CCA GCC ATG GCC GAT GTT TTG ATG ACC CAA ACT CC |
| 97 | CT GCC CAA CCA GCC ATG GCC GAC ATC CAG ATG ACC CAG TCT CC |
| 98 | CT GCC CAA CCA GCC ATG GCC GAT ATC CAG ATG ACA CAG ACT AC |
| 99 | CT GCC CAA CCA GCC ATG GCC GAC ATT GTG ATG ACC CAG TCT CC |
| 128 | CT GCC CAA CCA GCC ATG GCC AAC ATT GTG CTG ACC CAA TCT CC |
| 129 | CT GCC CAA CCA GCC ATG GCC GAT GTT GTG ATG ACC CAA ACT CC |
| 189 | CT GCC CAA CCA GCC ATG GCC GAA ATT GTG CTC ACC CAG TCT CC |
| 190 | CT GCC CAA CCA GCC ATG GCC AGT ATT GTG ATG ACC CAG ACT CC |
| 13 | CT GCC CAA CCA GCC ATG GCC GAT ATT GTG CTA ACT CAG TCT CC |
| 17 | CT GCC CAA CCA GCC ATG GCC CAA ATT GTT CTC ACC CAG TCT CC |
| 38 | CT GCC CAA CCA GCC ATG GCC GAC ATT CAG CTG ACC CAG TCT CC |
| 39 | CT GCC CAA CCA GCC ATG GCC GAT ATT GTG ATG ACC CAG GCT GC |
| 40 | CT GCC CAA CCA GCC ATG GCC GAC CTT GTG CTG ACA CAG TCT CC |
| 41 | CT GCC CAA CCA GCC ATG GCC GAA AAT GTG CTC ACC CAG TCT CC |
| 42 | CT GCC CAA CCA GCC ATG GCC GAA ACA ACT GTG ACC CAG TCT CC |
| 43 | CT GCC CAA CCA GCC ATG GCC GAT GCT GTG ATG ACC CAG ATT CC |
| 44 | CT GCC CAA CCA GCC ATG GCC GAC ATC TTG CTG ACT CAG TCT CC |
| 45 | CT GCC CAA CCA GCC ATG GCC GAT GTT GTG ATA ACT CAG GAT GA |
| 46 | CT GCC CAA CCA GCC ATG GCC GAT GTT GTG GTG ACT CAA ACT CC |
| 47 | CT GCC CAA CCA GCC ATG GCC AAC ATT GTG ATG GCC TGG TCT CC |
| 54 | CT GCC CAA CCA GCC ATG GCC TCA TTA TTG CAG GTG CTT GTG GG |
| 55 | CT GCC CAA CCA GCC ATG GCC GAT ATT GTG ATA ACC CAG GAT GA |
| 56 | CT GCC CAA CCA GCC ATC GCC GAC ATT GTG ATG ACC CAG TCT CA |
| 57 | CT GCC CAA CCA GCC ATG GCC GAA ATG GTT CTC ACC CAG TCT CC |
| 58 | CT GCC CAA CCA GCC ATG GCC GAT GTT GTG CTG ACC CAA ACT CC |
| 59 | CT GCC CAA CCA GCC ATG GCC GAC GTT GTG ATG TCA CAG TCT CC |
| 60 | CT GCC CAA CCA GCC ATG GCC GAC ATT GTG ACG TCA CAG TCT CC |
| 61 | CT GCC CAA CCA GCC ATG GCC CAA GTT GTT CTC ACC CAG TCT CC |
| 62 | CT GCC CAA CCA GCC ATG GCC GAC GTC CAG ATA ACC CAG TCT CC |

| PCR OLIGO FOR HC AND K ANTIBODIES | |
|---|---|
| 1 HC | GA TGG GGG TGT CGT TTT GGC |
| 2 K | AC AGT TGG TGC AGC ATC AGC |

*FIG. 2*

DNA Sequences of Oligos used to delete CDR1-CDR3 regions of 668-4

Kappa Chain

Framework 4                      Stop Stop Stop    Framework 1

TAT TTC CAG CTT GGT CCC|TCT AGA GTT AAC GAT ATC AA CGT|TTA|T|CTA|A|TCA|GCA AGA GAT GGA GGC TTG

Heavy Chain

Framework 4                      Stop Stop Stop    Framework 4

TGA GGT TCC TTG ACC CCA|CTG CAG AGT ACT AGG CCT CT GAG|CTA|C|TCA|G|TTA|GGT GAT TGA GTA GCC AGT

FIG. 4

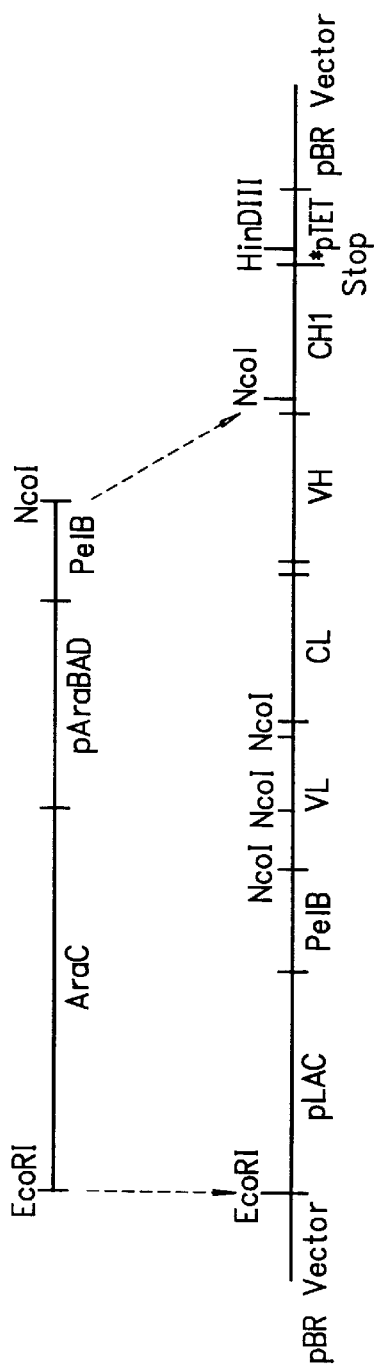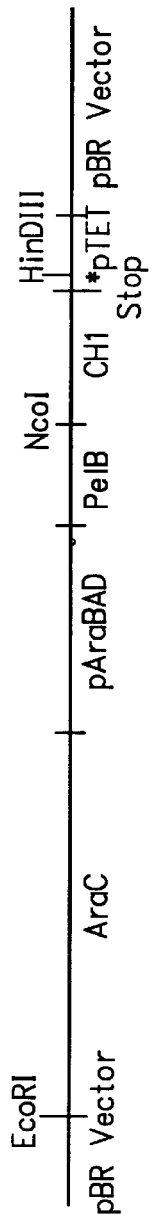
FIG. 5A
FIG. 5B
* represents 19 base pairs at the 5'-end of the tetracycline promoter removed by HinDIII digestion

POLYVALENT DISPLAY LIBRARIES

BACKGROUND OF THE INVENTION

Over recent years, many publications have reported the use of phage-display technology to produce and screen libraries of polypeptides for binding to a selected target. See, e.g, Cwirla et al., *Proc. Natl. Acad. Sci. USA* 87, 6378–6382 (1990); Devlin et al., *Science* 249, 404–406 (1990), Scott & Smith, *Science* 249, 386–388 (1990); Ladner et al., U.S. Pat. No. 5,571,698. A basic concept of phage display methods is the establishment of a physical association between DNA encoding a polypeptide to be screened and the polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target bind to the target and these phage are enriched by affinity screening to the target. The identity of polypeptides displayed from these phage can be determined from their respective genomes. Using these methods a polypeptide identified as having a binding affinity for a desired target can then be synthesized in bulk by conventional means.

Phage display technology has also been used to produce and screen libraries of heterodimeric proteins, such as Fab fragments. See e.g., Garrard et al., *Bio/Tech* 9, 1373–1377 (1991). Phage display libraries of Fab fragments are produced by expressing one of the component chains as a fusion with a coat protein, as for display of single-chain polypeptides. The partner antibody chain is expressed in the same cell from the same or a different replicon as the first chain, and assembly occurs within the cell. Thus, a phage-Fab fragment has one antibody chain fused to a phage coat protein so that it is displayed from the outersurface of the phage and the other antibody chain is complexed with the first chain.

In a further expansion of the basic approach, polypeptide libraries have been displayed from replicable genetic packages other than phage. These replicable genetic packages include eucaryotic viruses and bacteria. The principles and strategy are closely analogous to those employed for phage, namely, that nucleic acids encoding antibody chains or other polypeptides to be displayed are inserted into the genome of the package to create a fusion protein between the polypetides to be screened and an endogenous protein that is exposed on the cell or viral surface. Expression of the fusion protein and transport to the cell surface result in display of polypeptides from the cell or viral surface.

Although conventional display methods have achieved considerable success in isolating antibodies and other polypeptides with specific binding to selected targets, some inefficiencies and limitations remain. In conventional methods, many library members bind nonspecifically to the target or the solid phase bearing the target and are amplified along with specifically bound library members causing poor efficiency at each round of affinity selection. Not only can this waste time and effort in performing many rounds of affinity selection, but members bearing polypeptides having specific affinity are lost at each round. Selection is generally terminated when sufficient rounds of affinity selection have been performed to achieve a significant number of members bearing polypeptides with affinity for a target even though many nonspecifically binding members are still present. Clonal isolates are then picked and tested individually to reduce the risk of losing specific-binding members through further rounds of selection. Clonal isolates shown to bind specifically may then be cloned into an expression work for future analysis, and, large-scale production. Accordingly, only one or a few of library members bearing polypeptides with specific affinity for the target present in the original repertoire are ever isolated.

The present application provides inter alia novel methods that overcome these inefficiencies and difficulties, and produce new diagnostic and therapeutic reagents.

Commonly owned co-pending application Ser. Nos. 60/044,292, 08/835,159 and 08/832,935, all filed Apr. 4, 1997 describe related subject matter and are incorporated by reference in their entirety for all purposes.

SUMMARY OF THE INVENTION

In one aspect, the invention provides methods of producing a multivalent polypeptide display library. The starting material is a library of replicable genetic packages, such as phage. A member of such a library is capable of displaying from its outersurface a fusion protein comprising a polypeptide to be screened and a tag. The fusion protein is encoded by a segment of a genome of the package. The polypeptides vary between library members, as does the number of copies of the fusion protein displayed per library member. The tag is the same in different library members. The library is contacted with a receptor having a specific affinity for the tag under conditions whereby library members displaying at least two copies of the fusion protein are preferentially bound to immobilized receptor by multivalent bonds between the receptor and the at least two copies of the tag. Library members bound to the immobilized receptor are then separated from unbound library members to produce a sublibrary enriched relative to the library for members displaying at least two copies of the fusion protein. Polypeptides of particular interest are antibodies, particularly Fab fragments. Multivalent Fab phage display libraries can be produced as follows. The starting material is a library of phage in which a library member comprises a phage capable of displaying from its outersurface a fusion protein comprising a phage coat protein, an antibody light or heavy chain variable domain, and a tag. In at least some members, the antibody heavy or light chain is complexed with a partner antibody heavy or light chain variable domain chain, the complex forming a Fab fragment to be screened. The fusion protein and/or the partner antibody heavy or light chain are encoded by segment(s) of the genome of the phage. The number of copies of the fusion protein and the partner antibody chain displayed per phage vary between library members. The library or a fraction thereof is contacted with a receptor having a specific affinity for the tag under conditions whereby library members displaying at least two copies of the fusion protein are preferentially bound to immobilized receptor by multivalent bonds between the receptor and the at least two copies of the tag. Library members bound to the receptor are then separated from unbound library members to produce an sublibrary enriched relative to the library for members displaying at least two copies of the fusion protein. An alternative method of producing a multivalent Fab phage display library is as follows. The starting material is a library of phage in which a library member comprises a phage capable of displaying from its outersurface a fusion protein comprising a phage coat protein, and an antibody light or heavy chain variable domain. At least in some members, the antibody heavy or light chain is complexed with a partner antibody heavy or light chain variable domain chain fused to a tag, the complex forming a Fab fragment to be screened. The fusion protein and/or the partner antibody heavy or light chain fused to the tag are encoded by segment(s) of the genome of the phage. The number of copies of the fusion protein and the partner antibody chain displayed per phage vary between library members. The library or a fraction thereof is contacted with a receptor having a specific affinity for the tag under conditions whereby library members displaying at least two copies of the partner antibody chain are preferentially bound to immobilized receptor by multivalent bonds between the immobilized receptor and the at least two copies of the tag. Bound library members are separated from unbound library members to produce an sublibrary enriched relative to the library for members displaying at least two copies of the partner antibody chain.

Having produced a polyvalent phage display library, such as described above, it can be screened by contacting the library with a target lacking specific affinity for the tag moiety(ies) and separating library members bound to the target via their displayed polypeptides from unbound library members. DNA segments encoding polypeptides having specific affinity for a target can be subcloned in an expression vector, and the polypeptides expressed in host cells. Polypeptides can then, for example, be formulated with diagnostic or therapeutic excipients.

In another aspect, the invention provides libraries of nucleic acid segments encoding polyclonal polypeptides having specific affinity for a target. Such a library comprises least four different nucleic acid segments. At least 90% of segments in the library encode polypeptides showing specific affinity for a target and no library member constitutes more than 50% of the library. In some libraries, at least 95% of library members encode polypeptides having specific affinity for a target and no member constitutes more than 25% of the library. Some libraries have at least 100 different members. In some libraries, the segments are contained in a vector. In some libraries, the segment encode antibody chains. In some libraries, first and second segments are present, respectively encoding antibody heavy chains and partner antibody light chains, which can complex to form a Fab fragment. The first and second segments can be incorporated into the same or different vectors.

The invention further provides cell libraries in which a member cell contains a nucleic acid segment from a nucleic acid library, as described above. Such a library of cells can be propagated under conditions in which the DNA segments are expressed to produce polyclonal polypeptides.

The invention further provides methods of producing polyclonal polypeptides having specific affinity for a target. The starting material for such methods is a library of replicable genetic packages. A member comprises a replicable genetic package capable of displaying a polypeptide to be screened encoded by a genome of the package. The polypeptides vary between members. DNA encoding at least four different polypeptides of the library of replicable genetic packages is subcloned into an expression vector to produce modified forms of the expression vector. The modified forms of the expression vector are introduced into a host and expressed in the host producing at least four different polypeptides. At least 75% of modified forms of the expression vector encode polypeptides having specific affinity for a target and no modified form of the expression vector constitutes more than 50% of the total.

Polypeptides of particular interest are antibodies and these are typically displayed from a phage libraries. A typical member of such a library is a phage capable of displaying from its outersurface an antibody comprising an antibody heavy chain variable domain completed with an antibody light chain variable domain. Either the heavy or light chain variable domain is expressed as a fusion protein with a coat protein of the phage and either the heavy or light chain variable domain or both is/are encoded by the genome of the phage. The heavy and/or light chain varies between members. DNA encoding the heavy and/or light chain variable domains are subcloned from the phage library members into an expression vector to produce modified forms of the expression vector. The modified forms of the expression vector are introduced into a host and expressed to produced antibodies formed by the heavy and light chain variable domains of the phage library in the host. The antibodies are then released from the host to form an antibody library of at least four antibodies. At least 75% of modified forms of the expression vector encode antibodies with specific affinity for a target and no modified form of the expression vector constitutes more than 50% of the total.

Polyclonal libraries of antibodies and other polypeptides produced by the above methods can be incorporated into a diagnostic kit, or formulated for use as a diagnostic or therapeutic reagent.

BRIEF DESCRIPTION OF THE FIGURES

FIG. 1: Primers used for amplification of immunoglobulin heavy chains (SEQ ID NOS: 20–52).

FIG. 2: Primers used for amplification of immunoglobulin light chains (SEQ ID NOS: 53–83).

FIG. 3A shows a vector obtained from Ixsys, Inc. and described in Huse, WO 92/06204, which provides the starting material for producing the vectors shown in FIGS. 3B and 3C.
FIGS. 3B and 3C show the BS39 and BS45 vectors used in the present examples. The following abbreviations are used:
A. Nonessential DNA sequence later deleted.
B. Lac promoter and ribosome binding site.
C. Pectate lyase signal sequence.
D. Kappa chain variable region.
E. Kappa chain constant region.
F. DNA sequence separating kappa and heavy chain, includes ribosome binding site for heavy chain.
G. Alkaline phosphatase signal sequence.
H. Heavy chain variable region.
I. Heavy chain constant region including 5 amino acids of the hinge region.
J. Decapeptide DNA sequence.
K. Pseudo gene VIII sequence with amber stop codon at 5' end.
L. Nonessential DNA sequence that was later deleted.
M. Deleted kappa chain variable sequence with translational step sequences.
N. Polyhistidine (6 codons_ sequence.
O. Same as F above, but lacking the HindIII site.
P. Deleted heavy chain variable sequence with translational stop sequence.
Q. Pseudo gene VIII sequence without amber stop codon at 5' end.
R. Deleted kappa chain variable sequence with transcriptional stop sequence.

FIG. 4: Oligonucleotides used in vector construction (SEQ ID NOS: 84–85).

FIG. 5: Insertion of araC into pBR-based vector (FIG. 5A) and the resulting vector pBRnco (FIG. 5B).

DEFINITIONS

Figure 3:
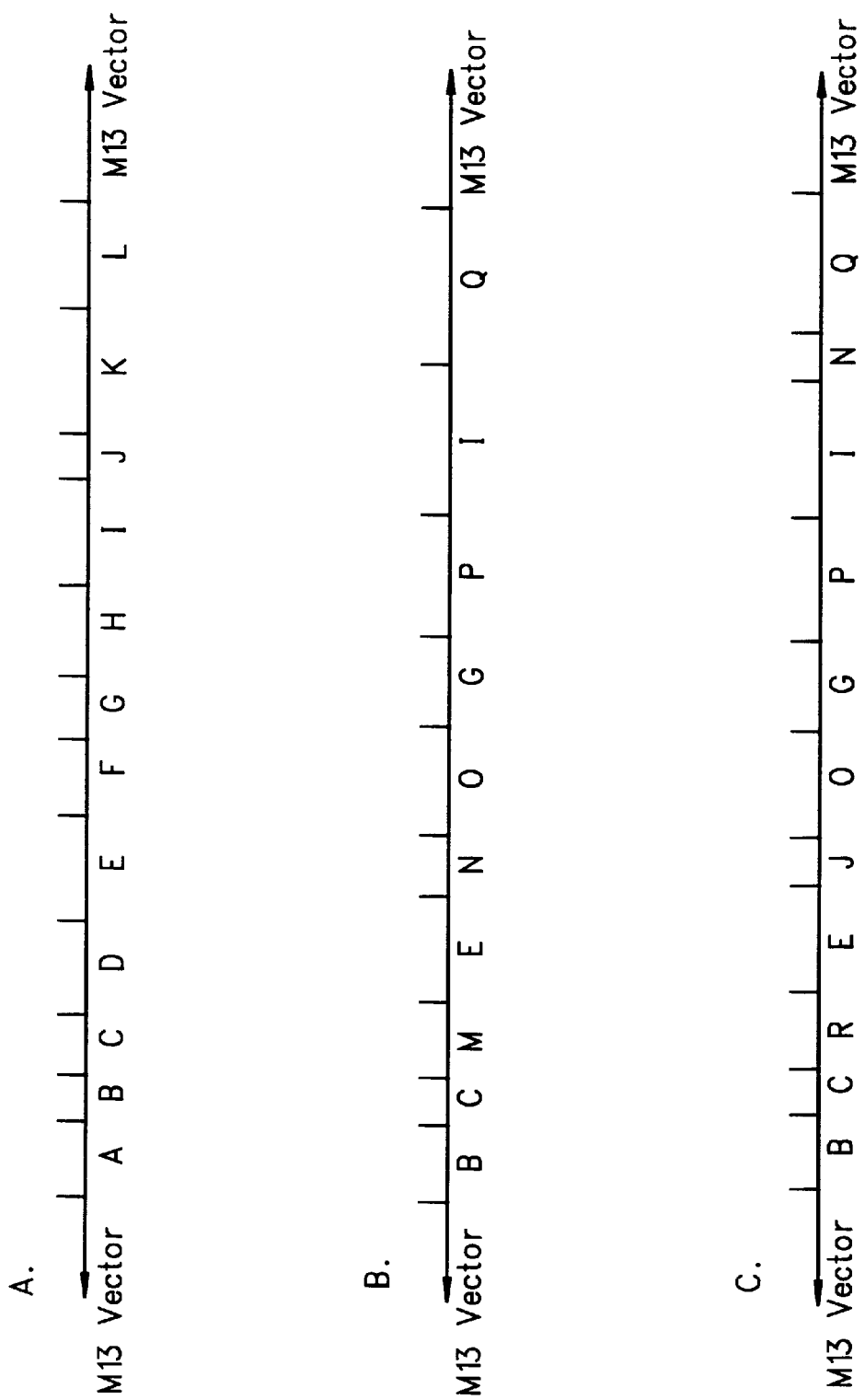
FIGS. 3(A–C): Vectors used for cloning antibodies.

Specific binding between an antibody or other binding agent and an antigen means a binding affinity of at least $10^6$ $M^{-1}$. Preferred binding agents bind with affinities of at least about $10^7$ $M^{-1}$, and preferably $10^8$ $M^{-1}$ to $10^9$ $M^{-1}$ or $10^{10}$ $M^{-1}$.

The term epitope means an antigenic determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

The basic antibody structural unit is known to comprise a tetramer. Each tetramer is composed of two identical pairs of polypeptide chains, each pair having one "light" (about 25 kDa) and one "heavy" chain (about 50–70 Kda). The amino-terminal portion of each chain includes a variable region of about 100 to 110 or more amino acids primarily responsible for antigen recognition. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 more amino acids. (See generally, *Fundamental Immunology* (Paul, W., ed., 2nd ed. Raven Press, New York, 1989), Ch. 7 (incorporated by reference in its entirety for all purposes).

The variable regions of each light/heavy chain pair form the antibody binding site. The chains all exhibit the same general structure of relatively conserved framework regions (FR) joined by three hypervariable regions, also called complementarily determining regions or CDRs. The CDRs from the two chains of each pair are aligned by the framework regions, enabling binding to a specific epitope. CDR and FR residues are delineated according to the standard sequence definition of Kabat et al., supra. An alternative structural definition has been proposed by Chothia et al., *J. Mol. Biol.* 196, 901–917 (1987); *Nature* 342, 878–883 (1989); and *J. Mol. Biol.* 186, 651–663 (1989).

The term antibody is used to mean whole antibodies and binding fragments thereof. Binding fragments include single chain fragments, Fv fragments and Fab fragments. The term Fab fragment is sometimes used in the art to mean the binding fragment resulting from papain cleavage of an intact antibody. The terms Fab' and F(ab')$_2$ are sometimes used in the art to refer to binding fragments of intact antibodies generated by pepsin cleavage. Here, Fab is used to refer generically to double chain binding fragments of intact antibodies having at least substantially complete light and heavy chain variable domains sufficient for antigen-specific bindings, and parts of the light and heavy chain constant regions sufficient to maintain association of the light and heavy chains. Usually, Fab fragments are formed by complexing a full-length or substantially full-length light chain with a heavy chain comprising the variable domain and at least the CH1 domain of the constant region.

An isolated species or population of species means an object species (e.g., binding polypeptides; of the invention) that is the predominant species present (i.e., on a molar basis it is more abundant than other species in the composition). Preferably, an isolated species comprises at least about 50, 80 or 90 percent (on a molar basis) of all macromolecular species present. Most preferably, the object species is purified to essential homogeneity (contaminant species cannot be detected in the composition by conventional detection methods). A target is any molecule for which it is desired to isolate partners with specific binding affinity for the target.

Targets of interest include antibodies, including antiidiotypic antibodies and autoantibodies present in autoimmune diseases, such as diabetes, multiple sclerosis and rheumatoid arthritis. Other targets of interest are growth factor receptors (e.g., FGFR, PDGFR, EFG, NGFR, and VEGF) and their ligands. Other targets are G-protein receptors and include substance K receptor, the angiotensin receptor, the α- and β-adrenergic receptors, the serotonin resceptors, and PAF receptor. See, e.g., Gilman, *Ann. Rev. Biochem.* 56, 625–649 (1987). Other targets include ion channels (e.g., calcium, sodium, potassium channels), muscarinic receptors, acetylcholine receptors, GABA receptors, glutamate receptors, and dopamine receptors (see Harpold, U.S. Pat. No. 5,401,629 and U.S. Pat. No. 5,436,128). Other targets are adhesion proteins such as integrins, selectins, and immunoglobulin superfamily members (see Springer, *Nature* 346, 425–433 (1990). Osborn, *Cell* 62, 3 (1990); Hynes, *Cell* 69, 11 (1992)). Other targets are cytokines, such as interleukins IL-1 through IL-13, tumor necrosis factors α & β, interferons α, β and γ, tumor growth factor Beta (TGF-β), colony stimulating factor (CSF) and granulocyte monocyte colony stimulating factor (GM-CSF). See *Human Cytokines: Handbook for Basic & Clinical Research* (Aggrawal et al. eds., Blackwell Scientific, Boston, Mass. 1991). Other targets are hormones, enzymes, and intracellular and intercellular messengers, such as, adenyl cyclase, guanyl cyclase, and phospholipase C. Drugs are also targets of interest. Target molecules can be human, mammalian or bacterial. Other targets are antigens, such as proteins, glycoproteins and carbohydrates from microbial pathogens, both viral and bacterial, and tumors. Still other targets are described in U.S. Pat. No. 4,366,241.

Display library members having full-length polypeptide coding sequences have coding sequences the same length as that of the coding sequences originally inserted into a display vector before propagation of the vector.

DETAILED DESCRIPTION

I. General

The present invention is directed to inter alia two related but self-sufficient improvements in conventional display methods. The first improvement provides methods of enriching conventional display libraries for members displaying more than one copy of a polypeptide prior to affinity screening of such libraries with a target of interest. Although practice of the claimed methods is not dependent on an understanding of mechanism, the rationale for these methods is believed to be that affinity selection of library members to immobilized binding partners occurs predominantly or exclusively through formation of multivalent bonds between multiple copies of displayed polypeptides on a library member and immobilized binding partners. Accordingly, only members of library displaying multiple copies of a polypeptide are capable of surviving affinity selection to immobilized binding partners. For example, conventional libraries of polypeptides fused to pVIII or a filamentous phage typically have Poisson distribution, in which most members display no copies of a polypeptide, a small proportion display one copy of a polypeptides, a still smaller proportion display two copies, and a still smaller proportion display three or more copies. The methods of the present invention enrich for the small proportion of conventional display libraries displaying two or more copies of a polypeptide. It is this rare fraction of conventional libraries that is capable of being affinity selected by immobilized binding partners.

Enrichment can be achieved by the inclusion of a tag as a component of the fusion protein from which polypeptides are displayed. The tag can be any polypeptide with a known receptor showing high binding specificity for the tag. The same tag is included in each member of the library. Enrichment is effected by screening the library for affinity binding to an immobilized receptor for the tag. Only library members having two or more copies of the tag are capable of binding to the immobilized receptor. By implication, library members having two copies of the tag have two copies of the fusion protein containing the tag, and two copies of a polypeptide to be screened. The library members that bind to the receptor thus constitute the small subpopulation of library members displaying two or more polypeptides. The library members not binding to the receptor are the majority of library members which display fewer than two copies of a polypeptide (i.e., zero or one copy). These library members, which would nonspecifically bind to the immobilized target in subsequent steps without contributing any members capable of surviving affinity screening through specific binding of the displayed polypeptide, can thus be substantially eliminated.

The bound library members, which display multiple copies of polypeptide, can then be subject to one or more rounds of affinity screening to any immobilized target of interest. Because most library members that would otherwise contribute to nonspecific binding have been eliminated before affinity screening to the target, each round of affinity screening typically results in a greater enrichment for library members with affinity for the target than would be the case in conventional methods. The greater degree of enrichment per round of screening allows adequate screening to be accomplished in fewer rounds and/or a greater proportion of the repertoire of specifically binding library members to be identified.

So efficient are the selection methods of the invention that they result in diverse populations in which the vast majority of members retaining full-length coding sequences encode polypeptides having specific affinity for the target. These polypeptides may differ in fine binding specificity within the target and binding affinity for the target.

A second aspect in which the invention represents a substantial departure from conventional methods resides in the subcloning of nucleic acids encoding displayed polypeptides of enriched libraries from a display vector to an expression vector without clonal isolation of individual members. The utility of transferring populations of coding sequences from a display vector to an expression vector without clonal isolation is realizable because the enriched libraries contain a high proportion of members having the desired binding specificity as described above.

Subcloning is achieved by excising or amplifying nucleic acids encoding polypeptides from the enriched library. The nucleic acids are then preferably size-fractionated on a gel and only full-length sequences are retained. The full-length sequences are inserted into an expression vector in operable linkage to appropriate regulatory sequences to ensure their expression. The modified expression vector is then introduced into appropriate host cells and expressed. Expression results in a population of polypeptides having specific affinity for the desired target. The population of polypeptides can be purified from the host cells by conventional methods. The population of polypeptides typically has substantially the same members in substantially the same proportions as were encoded by the enriched display library. As in the display library, the polypeptides typically differ in fine binding specificity, and binding affinity for the chosen target.

The populations of polypeptides can be used as diagnostic and therapeutic reagents. For example, if the target is a viral antigen, the polypeptides can be used to assay the presence of the virus in tissue samples. If the target is a tumor antigen, the polypeptides can be used as a therapeutic reagent to deliver a toxic substance to cells bearing the tumor antigen. The use of polyclonal preparation has advantages over a monoclonal reagent in both of these types of applications. For example, the diverse fine binding specificity of members of a population often allows the population to bind to several variant forms of target (e.g., species variants, escape mutant forms) to which a monoclonal reagent may be unable to bind.

II. Display Libraries

A. Replicable Genetic Packages

A replicable genetic package means a cell, spore or virus. The replicable genetic package can be eucaryotic or procaryotic. A display library is formed by introducing nucleic acids encoding exogenous polypeptides to be displayed into the genome of the replicable genetic package to form a fusion protein with an endogenous protein that is normally expressed from the outersurface of the replicable genetic package. Expression of the fusion protein, transport to the outersurface and assembly results in display of exogenous polypeptides from the outersurface of the genetic package.

The genetic packages most frequently used for display libraries are bacteriophage, particularly filamentous phage, and especially phage M13, Fd and F1. Most work has inserted libraries encoding polypeptides to be displayed into either gIII or gVIII of these phage forming a fusion protein. See, e.g., Dower, WO 91/19818; Devlin, WO 91/18989; MacCafferty, WO 92/01047 (gene III); Huse, WO 92/06204; Kang, WO 92/18619 (gene VIII). Such a fusion protein comprises a signal sequence, usually from a secreted protein other than the phage coat protein, a polypeptide to bus displayed and either the gene III or gene VIII protein or a fragment thereof. Exogenous coding sequences are often inserted at or near the N-terminus of gene III or gene VIII although other insertion sites are possible. Some filamentous phage vectors have been engineered to produce a second copy of either gene III or gene VIII. In such vectors, exogenous sequences are inserted into only one of the two copies. Expression of the other copy effectively dilutes the proportion of fusion protein incorporated into phage particles and can be advantageous in reducing selection against polypeptides deleterious to phage growth. In another variation, exogenous polypeptide sequences are cloned into phagemid vectors which encode a phage coat protein and phage packaging sequences but which are not capable of replication. Phagemids are transfected into cells and packaged by infection with helper phage. Use of phagemid system also has the effect of diluting fusion proteins formed from coat protein and displayed polypeptide with wildtype copies of coat protein expressed from the helper phage. See, e.g., Garrard, WO 92/09690.

Eucaryotic viruses can be used to display polypeptides in an analogous manner. For example, display of human heregulin fused to gp70 of Moloney murine leukemia virus has been reported by Han et al., *Proc. Natl. Acad. Sci. USA*

92, 9747–9751 (1995). Spores can also be used as replicable genetic packages. In this case, polypeptides are displayed from the outersurface of the spore. For example, spores from *B. subtilis* have been reported to be suitable. Sequences of coat proteins of these spores are provided by Donovan et al., *J. Mol. Biol.* 196, 1–10 (1987). Cells can also be used as replicable genetic packages. Polypeptides to be displayed are inserted into a gene encoding a cell protein that is expressed on the cells surface. Bacterial cells including *Salmonella typhimurium, Bacillus subtilis, Pseudomonas aeruginosa, Vibrio cholerae, Klebsiella pneumonia, Neisseria gonorrhoeae, Neisseria meningitidis, Bacteroides nodosus, Moraxella bovis,* and especially *Escherichia coli* are preferred. Details of outersurface proteins are discussed by Ladner et al., U.S. Pat. No. 5,571,698, and Georgiou et al., *Nature Biotechnology* 15, 29–34 (1997) and references cited therein. For example, the lamB protein of *E. coli* is suitable.

B. Displayed Polypeptides

Polypeptides typically displayed from replicable genetic packages fall into a number of broad categories. One category is libraries of short random or semi random peptides. See, e.g., Cwirla et al., supra. The strategy here is to produce libraries of short peptides in which some or all of the positions are systematically varied for the different amino acids. Random peptide coding sequences can be formed by the cloning and expression of randomly-generated mixtures of oligonucleotides is possible in the appropriate recombinant vectors. See, e.g., Oliphant et al., *Gene* 44;177–183 (1986) A second category of library comprises variants of a starting framework protein. See Ladner et al., supra. In this approach, a starting polypeptide which may be of substantial length is chosen and only selected positions are varied. The nucleic acid encoding the starting polypeptide can be mutagenized by, for example, insertion of mutagenic cassette(s) or error-prone PCR.

A third category of library consists of antibody libraries. Antibody libraries can be singles or double chain. Single chain antibody libraries can comprise the heavy or light chain of an antibody alone or the variable domain thereof. However, more typically, the members of single-chain antibody libraries are formed from a fusion of heavy and light chain variable domains separated by a peptide spacer within a single contiguous protein. See e.g., Ladner et al., WO 88/06630; McCafferty et al., WO 92/01047. Double-chain antibodies are formed by noncovalent association of heavy and light chains or binding fragments thereof. The diversity of antibody libraries can arise from obtaining antibody-encoding sequences from a natural source, such as a nonclonal population of immunized or unimmunized B cells. Alternatively, or additionally, diversity can be introduced by artificial mutagenesis as discussed for other proteins.

Nucleic acids encoding polypeptides to be displayed optionally flanked by spacers are inserted into the genome of a replicable genetic package as discussed above by standard recombinant DNA techniques (see generally, Sambrooke et al., *Molecular Cloning, A Laboratory Manual,* 2d ed., Cold Spring Harbor Laboratory Press, Cold Spring Harbor, N.Y., 1989, incorporated by reference herein). The nucleic acids are ultimately expressed as polypeptides (with or without spacer or framework residues) fused to all or part of the an outersurface protein of the replicable package. Libraries often have sizes of about $10^3$, $10^4$, $10^6$, $10^7$, $10^8$ or more members.

C. Double-Chain Antibody Display Libraries

Double-chain antibody display libraries represent a species of the replicable genetic display libraries discussed above. Production of such libraries is described by, e.g., Dower, U.S. Pat. No. 5,427,908; Huse WO 92/06204; Huse, in *Antibody Engineering,* (Freeman 1992), Ch. 5; Kang, WO 92/18619; Winter, Wo 92/20791; McCafferty, WO 92/01047; Hoogenboom WO 93/06213; Winter et al., *Annu. Rev. Immunol.* 12, 433–455 (1994); Hoogenboom et al., *Immunological Reviews* 130, 41–68 (1992); Soderlind et al., *Immunological Reviews* 130, 109–124 (1992). In double-chain antibody libraries, one antibody chain is fused to a phage coat protein, as is the case in single chain libraries. The partner antibody chain is complexed with the first antibody chain, but the partner is not directly linked to a phage coat protein. Either the heavy or light chain can be the chain fused to the coat protein. Whichever chain is not fused to the coat protein is the partner chain. This arrangement is typically achieved by incorporating nucleic acid segments encoding one antibody chain gene into either gIII or gVIII of a phage display vector to form a fusion protein comprising a signal sequence, an antibody chain, and a phage coat protein. Nucleic acid segments encoding the partner antibody chain can be inserted into the same vector as those encoding the first antibody chain. Optionally, heavy and light chains can be inserted into the same display vector linked to the same promoter and transcribed as a polycistronic message. Alternatively, nucleic acids encoding the partner antibody chain can be inserted into a separate vector (which may or may not be a phage vector). In this case, the two vectors are expressed in the same cell (see WO 92/20791). The sequences encoding the partner chain are inserted such that the partner chain is linked to a signal sequence, but is not fused to a phage coat protein. Both antibody chains are expressed and exported to the periplasm of the cell where they assemble and are incorporated into phage particles.

Antibody encoding sequences can be obtained from lymphatic cells of a human or nonhuman animal. Often the cells have been immunized, in which case immunization can be performed in vivo before harvesting cells, or in vitro after harvesting cells, or both. Spleen cells of an immunized animal are a preferred source material. Immunization of humans is only possible with certain antigens. The number of different H chain genes and L chain genes in a spleen from an immunized animal is about $10^6$, which can be assembled in $10^{12}$ potential combinations.

Rearranged immunoglobulin genes c-an be cloned from genomic DNA or mRNA. For the latter, mRNA is extracted from the cells and cDNA is prepared using reverse transcriptase and poly dT oligonucleotide primers. Primers for cloning antibody encoding sequences are discussed by Larick et al., *Bio/Technology* 7, 934 (1989), Danielsson & Borrebaceick, in *Antibody Engineering: A Practical Guide* (Freeman, New York, 1992), p. 89 and Huse, id. at Ch. 5.

Repertoires of antibody fragments have been constructed by combining amplified VH and VL sequences together in several ways. Light and heavy chains can be inserted into different vectors and the vectors combined in vitro (Hogrefe et al., *Gene* 128, 119–126 (1993)) or in vivo (Waterhouse et al., *Nucl. Acids. Res.* 21, 2265–66 (1993)). Alternatively, the light and heavy chains can be cloned sequentially into the same vector (Barbas et al., *Proc. Natl. Acad. Sci. USA* 88, 7987–82 (1991)) or assembled together by PCR and then inserted into a vector (Clackson et al., *Nature* 352, 624–28 (1991)). Repertoires of heavy chains can be also be combined with a single light chain or vice versa. Hoogenboom et al., *J. Mol. Biol.* 227, 381–88 (1992).

Some exemplary vectors and procedures for cloning populations of heavy chain and light chain encoding sequences have been described by Huse, WO 92/06204. Diverse populations of sequences encoding Hc polypeptides are cloned into M13IX30 and sequences encoding Lc polypeptides are cloned into M13IX11. The populations are inserted between the XhoI-SeeI or StuI restriction enzyme sites in M13IX30 and between the SacI-XbaI or EcoRV sites in M13IX11 (FIGS. 1A and B of Huse, respectively). Both vectors contain two pairs of MluI-HindIII restriction enzyme sites (FIGS. 1A and B of Huse) for joining together the Hc and Lc encoding sequences and their associated vector sequences. The two pairs are symmetrically orientated about the cloning site so that only the vector proteins containing the sequences to be expressed are exactly combined into a single vector.

Others exemplary vectors and procedures for cloning antibody chains into filamentous phage are described in the present Examples.

III. Enrichment for Polyvalent Display Members

A. Theory of the Method

That members of a library displaying multiple copies of a polypeptide are comparatively rare in display libraries is a finding apparently at variance with some early reports in the field. See, e.g., Cwirla et al., supra. Most work on display libraries has been done by inserting nucleic acid libraries into pIII or pVIII of filamentous phage. Because pIII is present in 4 or 5 copies per phage and pVIII is present in several hundred copies per phage, some early reports assumed that foreign polypeptides would be displayed in corresponding numbers per phage. However, more recent work has made clear that the actual number of copies of polypeptide displayed per phage is well below theoretical expectations, perhaps due to proteolytic cleavage of polypeptides. Winter et al., *Ann. Rev. Immunol.* 12, 433–55 (1994). Further, vector systems used for phage display often encode two copies of a phage coat protein, one of which is a wildtype protein and the other of which forms a fusion protein with exogenous polypeptides to be displayed. Both copies are expressed and the wildtype coat protein effectively dilutes the representation of the fusion protein in the phage coat.

A typical ratio of displayed Fabs per phage, when Fabs are expressed from pVIII of a filamentous phage is about 0.2. The probability, Pr(y), of y Fabs being expressed on a phage particle if the average frequency of expression per phage is n is given by the Poisson probability distribution $$Pr(y)=e^{-n}n^y/y!$$

For a frequency of 0.2 Fabs per phage, the probabilities for the expression of 0, 1, 2, and 3 Fabs per phage are 0.82, 0.16, 0.016, and 0.0011. The proportion of phage particle displaying two or more Fabs is therefore only 0.017.

The low representation of members displaying more than one Fab fragment in a phage display library can be related to the present inventors' result that only a small percentage of such library members are capable of surviving affinity selection to immobilized binding partners. A library was constructed in which all members encodes the same Fab fragment which was known to have a high binding affinity for a particular target. It was found that even under the mildest separation conditions for removal of free from bound phage, it was not possible to bind more than about 0.004 of the total phage. This proportion is the same order of magnitude as the proportion of phage displaying at least two Fab fragments, suggesting that phage must display at least two Fab fragments to bind to immobilized target. Probably shear forces dissociate phage displaying only a single Fab fragment from the solid phase. Therefore, at least two binding events are necessary for a phage-Fab library member to be bound to immobilized target with sufficient avidity to enable separation of the bound from the free phage. It is expected that similar constraints apply in other forms of display library.

The strategy of the present invention is to enrich for library members displaying more than one polypeptide before the library is contacted with a screening target. Library members lacking two or more polypeptides, which are incapable of surviving affinity via binding through displayed polypeptides to any immobilized screening target, but which nevertheless can survive affinity selection by formation of multiple nonspecific bonds to such a target or its support, are thus substantially eliminated before screening of the library to target is performed.

B. Tags and Receptors

The above strategy is effected by the use of paired tags and receptors. A tag is typically a short peptide sequence and a receptor is any agent that shows specific but reversible binding for the tag and can be immobilized to a support. Suitable tag-receptor combinations include epitope and antibody; for example, many high affinity hexapeptide ligands are known for the anti-dynorphin mAb 32.39, (see Barrett et al., *Neuropeptides* 6, 113–120 (1985) and Cull et al., *PNAS* 89, 1865–1869 (1992)) and a variety of short peptides are known to bind the MAb 3E7 (Schatz, *Biotechnology* 11, 1138–43 (1993)). Another combination of tag and antibody is described by Blanar & Rutter, *Science* 256, 1014–1018 (1992).

Another example of a tag-receptor pair is the FLAG™ system (Kodak). The FLAG™ molecular tag consists of an eight amino acid FLAG peptide marker that is linked to the target binding moiety. A 24 base pair segment containing a FLAG coding sequence can be inserted adjacent to a nucleotide sequence that codes for the displayed polypeptide. The FLAG peptide includes an enterokinase recognition site that corresponds to the carboxy-terminal five amino acids. Capture moieties suitable for use with the FLAG peptide marker include antibodies Anti-FLAG M1, M2 and M5, which are commercially available.

Still other combinations of peptides and antibodies can be identified by conventional phage display methods. Further suitable combinations of peptide sequence and receptor include polyhistidine and metal chelate ligands containing $Ni^{2+}$ immobilized on agarose (see Hochuli in *Genetic Engineering: Principles and Methods* (ed. J K Setlow, Plenum Press, New York), Ch. 18, pp. 87–96 and maltose binding protein (Maina et al., *Gene* 74, 365–373 (1988)).

Receptors are often labelled with biotin allowing the receptors to be immobilized to an avidin-coated support. Biotin labelling can be performed using the biotinylating enzyme, BirA (see, e.g., Schatz, *Biotechnology* 11, 1138–43 (1993)).

A nucleic acid sequence encoding a tag is inserted into a display vector in such a manner that the tag is expressed as part of the fusion protein containing the polypeptide to be displayed and an outersurface protein of the replicable genetic package. The relative ordering of these components is not critical provided that the tag and polypeptide to be displayed are both exposed on the outersurface of the package. For example, the tag can be placed between the outersurface protein and the displayed polypeptide or at or near the exposed end of the fusion protein.

In replicable genetic packages displaying Fabs, a tag can be fused to either the heavy or the light Fab chain, irrespective which chain is linked to a phage coat protein. Optionally, two different tags can used one fused to each of the heavy and light chains. One tag is usually positioned between the phage coat protein and antibody chain linked thereto, and the other tag is positioned at either the N- or C-terminus of the partner chain.

C. Selection of Polyvalent Members

Selection of polyvalent library members is performed by contacting the library with the receptor for the tag component of library members. Usually, the library is contacted with the receptor immobilized to a solid phase and binding of library members through their tag to the receptor is allowed to reach equilibrium. The complexed receptor and library members are then brought out of solution by addition of a solid phase to which the receptor bears affinity (e.g., an avidin-labelled solid phase can be used to immobilize biotin-labelled receptors). Alternatively, the library can be contacted with receptor in solution and the receptor subsequently immobilized. The concentration of receptor should usually be at or above the Kd of the tag/receptor during solution phase binding so that most displayed tags bind to a receptor at equilibrium. When the receptor-library members are contacted with the solid phase only the library members linked to receptor through at least two displayed tags remain bound to the solid phase following separation of the solid phase from library members in solution. Library members linked to receptor through a single tag are presumably sheared from the solid phase during separation and washing of the solid phase. After removal of unbound library members, bound library members can be dissociated from the receptor and solid phase by a change in ionic strength or pH, or addition of a substance that competes with the tag for binding to the receptor. For example, binding of metal chelate ligands immobilized on agarose and containing $Ni^{2+}$ to a hexahistidine sequence is easily reversed by adding imidazole to the solution to compete for binding of the metal chelate ligand. Antibody-peptide binding can often be dissociated by raising the pH to 10.5 or higher.

The average number of polypeptides per library member selected by this method is affected by a number of factors. Decreasing the concentration of receptor during solution-phase binding has the effect of increasing the average number of polypeptides in selected library members. An increase in the stringency of the washing conditions also increases the average number of polypeptides per selected library member. The physical relationship between library members and the solid phase can also be manipulated to increase the average number of polypeptides per library member. For example, if discrete particles are used as the solid phase, decreasing the size of the particles increases the steric constraints of binding and should require a higher density of polypeptides displayed per library member.

For Fab libraries having two tags, one linked to each antibody chain, two similar rounds of selection can be performed, with the products of one round becoming the starting materials for the second round. The first round of selection is performed with a receptor to the first tag, and the second round with a receptor to the second tag. Selecting for both tags enriches for library members displaying two copies of both heavy and light antibody chains (i.e., two Fab fragments).

D. Selection For Affinity to Target

Library members enriched for polyvalent display of Fabs or other polypeptides are screened for binding to a target. The target can be any molecule of interest for which it is desired to identify binding partners. The target should lack specific binding affinity for the tag(s), because in this step it is the displayed polypeptides being screened, and not the tags that bind to the target. The screening procedure at this step is closely analogous to that in the previous step except that the affinity reagent is a target of interest rather than a receptor to a tag. The enriched library members are contacted with the target which is usually labelled (e.g., with biotin) in such a manner that allows its immobilization. Binding is allowed to proceed to equilibrium and then target is brought out of solution by contacting with the solid phase in a process known as panning (Parmley & Smith, *Gene* 73, 305–318 (1988)). Library members that remain bound to the solid phase throughout the selection process do so by virtue of polyvalent bonds between them and immobilized target molecules. Unbound library members are washed away from the solid phase.

Usually, library members are subject to amplification before performing a subsequent round of screening. Often, bound library members can be amplified without dissociating them from the support. For example, gene VIII phage library members immobilized to beads, can be amplified by immersing the beads in a culture of *E. coli.* Likewise, bacterial display libraries can be amplified by adding growth media to bound library members. Alternatively, bound library members can be dissociated from the solid phase (e.g., by change of ionic strength or pH) before performing subsequent selection, amplification or propagation.

After affinity selection, bound library members are now enriched for two features: multivalent display of polypeptides and display of polypeptides having specific affinity for the target of interest. However, after subsequent amplification, to produce a secondary library, the secondary library remains enriched for display of polypeptides having specific affinity for the target, but, as a result of amplification, is no longer enriched for polyvalent display of polypeptides. Thus, a second cycle of polyvalent enrichment can then be performed, followed by a second cycle of affinity enrichment to the screening target. Further cycles of affinity enrichment to the screening target, optionally, alternating with amplification and enrichment for polyvalent display can then be performed, until a desired degree of enrichment has been performed.

In a variation, affinity screening to a target is performed in competition with a compound that resembles but is not identical to the target. Such screening preferentially selects for library members that bind to a target epitope not present on the compound. In a further variation, bound library members can be dissociated from the solid phase in competition with a compound having known crossreactivity with a target for an antigen. Library members having the same or similar binding specificity as the known compound relative to the target are preferentially eluted. Library members with affinity for the target through an epitope distinct from that recognized by the compound remain bound to the solid phase.

Discrimination in selecting between polypeptides of different monovalent affinities for the target is affected by the valency of library members and the concentration of target during the solution phase binding. Assuming a minimum of i labeled target molecules must be bound to a library member to immobilize it on a solid phase, then the probability of immobilization can be calculated for a library member displaying n polypeptides. From the law of mass action, the bound/free polypeptide fraction and the bound/polypeptide fraction, F, is $K[targ]/(1+K[targ])$, where $[targ]$ is the total target concentration in solution. Thus, the probability that i or more displayed polypeptides per library member are bound by the labeled target ligand is given by the binomial probability distribution:

$$\sum_{y=i}^{n} (n!/[y!(n-y)!]F^y(1-F)^{n-y}$$

As the probability is a function of K and [target], multivalent display members each having a monovalent affinity, K, for the target can be selected by varying the concentration of target. The probabilities of solid-phase immobilization for i=1, 2, or 3, with library members exhibiting monovalent affinities of 0.1/[Ag], 1/[Ag], and 10/[Ag], and displaying n polypeptides per member are:

| n  | K = 0.1/[targ] | K = 1/[targ] | K = 10/[targ] |
|----|---------------|--------------|---------------|
| Probability of Immobilization (i = 1) ||||
| 1  | 0.09    | 0.5   | 0.91  |
| 2  | 0.17    | 0.75  | 0.99  |
| 3  | 0.25    | 0.875 |       |
| 4  | 0.32    | 0.94  |       |
| 5  | 0.38    | 0.97  |       |
| 6  | 0.44    | 0.98  |       |
| 7  | 0.49    | 0.99  |       |
| 8  | 0.53    |       |       |
| 9  | 0.58    |       |       |
| 10 | 0.61    |       |       |
| 20 | 0.85    |       |       |
| 50 | 0.99    |       |       |
| Probability of Immobilization (i = 2) ||||
| 2  | 0.008   | 0.25  | 0.83  |
| 3  | 0.023   | 0.50  | 0.977 |
| 4  | 0.043   | 0.69  | 0.997 |
| 5  | 0.069   | 0.81  |       |
| 6  | 0.097   | 0.89  |       |
| 7  | 0.128   | 0.94  |       |
| 8  | 0.160   | 0.965 |       |
| 9  | 0.194   | 0.98  |       |
| 20 | 0.55    |       |       |
| 50 | 0.95    |       |       |
| Probability of Immobilization (i = 3) ||||
| 3  | 0.00075 | 0.125 | 0.75  |
| 4  | 0.0028  | 0.31  | 0.96  |
| 5  | 0.0065  | 0.50  | 0.99  |
| 6  | 0.012   | 0.66  |       |
| 7  | 0.02    | 0.77  |       |
| 8  | 0.03    | 0.855 |       |
| 9  | 0.0415  | 0.91  |       |
| 10 | 0.055   | 0.945 |       |
| 12 | 0.089   | 0.98  |       |
| 14 | 0.128   | 0.99  |       |
| 20 | 0.27    |       |       |
| 50 | 0.84    |       |       |

The above tables show that the discrimination between immobilizing polypeptides of different monovalent binding affinities is affected by the valency of library members (n) and by the concentration of target for the solution binding phase. Discrimination is maximized when n (number of polypeptides displayed per phage) is equal to i (minimum valency required for solid phase binding). Discrimination is also increased by lowering the concentration of target during the solution phase binding. Usually, the target concentration is around the Kd of the polypeptides sought to be isolated. Target concentration of $10^{-8}$–$10^{-10}$ M are typical.

Enriched libraries produced by the above methods are characterized by a high proportion of members encoding polypeptides having specific affinity for the target. For example, at least 10, 25, 50, 75, 95, or 99% of members encode polypeptides having specific affinity for the target. The exact percentage of members having affinity for the target depends whether the library has been amplified following selection, because amplification increases the representation of genetic deletions. However, among members with full-length polypeptide coding sequences, the proportion encoding polypeptides with specific affinity for the target is very high (e.g., at least 50, 75, 95 or 99%). Not all of the library members that encode a polypeptide with specific affinity for the target necessarily display the polypeptide. For example, in a library in which 95% of members with full-length coding sequences encode polypeptides with specific affinity for the target, usually fewer than half actually display the polypeptide. Usually, such libraries have at least 4, 10, 20, 50, 100, 1000, 10,000 or 100,000 different coding sequences. Usually, the representation of any one such coding sequences is no more than 50%, 25% or 10% of the total coding sequences in the library.

IV. Polyclonal Libraries

A. Production

The nucleic acid sequences encoding displayed polypeptides such as are produced by the above methods can be subcloned directly into an expression vector without clonal isolation and testing of individual members. Generally, the sequence encoding the outersurface protein of the display vector fused to displayed polypeptides is not excised or amplified in this process. The nucleic acids can be excised by restriction digestion of flanking sequences or can be amplified by PCR using primers to sites flanking the coding sequences. See generally *PCR Technology: Principles and Applications for DNA Amplification* (ed. H. A. Erlich, Freeman Press, New York, N.Y., 1992); *PCR Protocols: A Guide to Methods and Applications* (eds. Innis, et al., Academic Press, San Diego, Calif., 1990); Mattila et al., *Nucleic Acids Res.* 19:4967 (1991); Eckert et al., *PCR Methods and Applications* 1:17 (1991); *PCR* (eds. McPherson et al., IRL Press, Oxford). PCR primers can contain a marker sequence that allows positive selection of amplified fragments when introduced into an expression vector. PCR primers can also contain restriction sites to allow cloning into an expression vector, although this is not necessary. For Fab libraries, if heavy and light chains are inserted adjacent or proximate to each other in a display vector, the two chains can be amplified or excised together. For some Fab libraries, only the variable domains of antibody chain(s) are excised or amplified. If the heavy or light chains of a Fab library are excised or amplified separately, they can subsequently be inserted into the same or different expression vectors.

Having excised or amplified fragments encoding displayed polypeptides, the fragments are usually size-purified on an agarose gel or sucrose gradient. Typically, the fragments run as a single sharp full-length band with a smear at lower molecular corresponding to various deleted forms of coding sequence. The band corresponding to full-length coding sequences is removed from the gel or gradient and these sequences are used in subsequent steps.

The next step is to join the nucleic acids encoding full-length coding sequences to an expression vector thereby creating a population of modified forms of the expression vector bearing different inserts. This can be done by conventional ligation of cleaved expression vector with inserts cleaved to have compatible ends. Alternatively, the use of restriction enzymes on insert DNA can be avoided. This method of cloning is beneficial because naturally encoded restriction enzyme sites may be present within insert sequences, thus, causing destruction of this sequence when treated with a restriction enzyme. For cloning without restricting, the insert and linearized vector sequences are treated briefly with a 3' to 5' exonuclease such as T4 DNA polymerase or exonuclease III. See Sambrook et al., *Molecular Cloning, A Laboratory Manual* (2nd Ed., CSHP, New York 1989). The protruding 5' termini of the insert generated by digestion are complementary to single-stranded overhangs generated by digestion of the vector. The overhangs are annealed, and the reannealed vector transfected into recipient host cells. The same result can be accomplished using 5' to 3' exonucleases rather than a 3' to 5' exonuclease.

Preferably, ligation of inserts to expression vector is performed under conditions that allow selection against reannealed vector and uncut vector. A number of vectors containing conditional lethal genes that allow selection against reannealed vector under nonpermissive conditions are known. See, e.g., Conley & Saunders, *Mol. Gen. Genet.* 194, 211–218 (1984). These vectors effectively allow positive selection for vectors having received inserts. Selection can also be accomplished by cleaving an expression vector in such a way that a portion of a positive selection marker (e.g., antibiotic resistance) is deleted. The missing portion is then supplied by full-length inserts. The portion can be introduced at the 3' end of polypeptide coding sequences in the display vector, or by included in a primer used for amplification of the insert. An exemplary selection scheme, in which inserts supply a portion of a tetracycline-resistance gene promoter deleted by HindIII cleavage of a pBR-derivative vector, is described in Example 17.

The choice of expression vector depends on the intended host cells in which the vector is to be expressed. Typically, the vector includes a promoter and other regulatory sequences in operable linkage to the inserted coding sequences that ensure the expression of the latter. Use of an inducible promoter is advantageous to prevent expression of inserted sequences except under inducing conditions. Inducible promoters include arabinose, lacZ, metallothionein promoter or a heat shock promoter. Cultures of transformed organisms can be expanded under noninducing conditions without biasing the population for coding sequences whose expression products are better tolerated by the host cells. The vector may also provide a secretion signal sequence position to form a fusion protein with polypeptides encoded by inserted sequences, although often inserted polypeptides are linked to a signal sequences before inclusion in the vector. Vectors to be used to receive sequences encoding antibody light and heavy chain variable domains sometimes encode constant regions or parts thereof that can be expressed as fusion proteins with inserted chains thereby leading to production of intact antibodies or fragments thereof.

*E. coli* is one prokaryotic host useful particularly for cloning the polynucleotides of the present invention. Other microbial hosts suitable for use include bacilli, such as *Bacillus subtilis*, and other enterobacteriaceae, such as Salmonella, Serratia, and various Pseudomoras species. In these prokaryotic hosts, one can also make expression vectors, which will typically contain expression control sequences compatible with the host cell (e.g., an origin of replication). In addition, any number of a, variety of well-known promoters will be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation.

Other microbes, such as yeast, are also be used for expression. Saccharomyces is a preferred host, with suitable vectors having expression control sequence, such as promoters, including 3-phosphoglycerate kinase or other glycolytic enzymes, and an origin of replication, termination sequences and the like as desired.

Mammalian tissue cell culture can also be used to express and produce the polypeptides of thus present invention (see Winnacker, *From Genes to Clones* (VCH Publishers, New York, N.Y., 1987). A number of suitable host cell lines capable of secreting intact immunoglobulins have been developed including the CHO cell lines, various Cos cell lines, HeLa cells, myeloma cell lines, transformed B-cells and hybridomas. Expression vectors for these cells can include expression control sequences, such as an origin of replication, a promoter, and an enhancer (Queen et al., *Immunol. Rev.* 89:49–68 (1986)), and necessary processing information sites, such as ribosome binding sites, RNA splice sites, polyadenylation sites, and transcriptional terminator sequences. Preferred expression control sequences are promoters derived from immunoglobulin genes, SV40, adenovirus, bovine papilloma virus, or cytomegalovirus.

Methods for introducing vectors containing the polynucleotide sequences of interest vary depending on the type of cellular host. For example, calcium chloride transfection is commonly utilized for prokaryotic cells, whereas calcium phosphate treatment or electroporation may be used for other cellular hosts. (See generally Sambrook et al., supra).

Once expressed collections of antibodies or other polypeptides are purified from culture media and host cells. Usually, polypeptides are expressed with signal sequences and are thus released to the culture media. However, if polypeptides are not naturally secreted by host cells, the polypeptides can be released by treatment with mild detergent. Polypeptides can then be purified by conventional methods including ammonium sulfate precipitation, affinity chromatography to immobilized target, column chromatography, gel electrophoresis and the like (see generally *Scopes, Protein Purification* (Springer-Verlag, New York, 1982)).

B. Characteristics of Libraries

The above methods result in novel libraries of nucleic acid sequences encoding polypeptides having specific affinity for a chosen target. The libraries of nucleic acids typically have at least 5, 10, 20, 50, 100, 1000, $10^4$ or $10^5$ different members. Usually, no single member constitutes more than 25 or 50% of the total sequences in the library. Typically, at least 75, 90, 95, 99 or 99.9% of library members encode polypeptides with specific affinity for the target molecules. The nucleic acid libraries can exist in free form, as components of any vector or transfected as a component of a vector into host cells.

The nucleic acid libraries can be expressed to generate polyclonal libraries of antibodies or other polypeptides having specific affinity for a target. The composition of such libraries is determined from the composition of the nucleotide libraries. Thus, such libraries typically have at least 5, 10, 20, 50, 100, 1000, $10^4$ or $10^5$ members with different amino acid composition. Usually, no single member constitutes more than 25 or 50% of the total polypeptides in the library. In some libraries, at least 75, 90, 95, 99 or 99.9% of polypeptides have specific affinity for the target molecules. The different polypeptides differ from each other in terms of fine binding specificity and affinity for the target.

V. Diagnostic and Therapeutics Uses

The use of polyclonal antibodies in diagnostics and therapeutics has been limited by the inability to generate preparations that have a well-defined affinity and specificity. Monoclonal antibodies developed using hybridoma technology do have well-defined specificity and affinity, but the selection process is often long and tedious. Further, a single monoclonal antibody does not meet all of the desired specificity requirements. Formation of polyclonal mixtures by isolation, and characterization of individual monoclonal antibodies, which are then mixed would be time consuming process which would increase in proportion to the number of monoclonal, included in the mixture and become prohibitive for substantial numbers of monoclonals. The polyclonal libraries of antibodies and other polypeptides having specificity for a given target produced by the present methods avoid these difficulties, and provide reagents that are useful in many therapeutic and diagnostic applications.

The use of polyclonals has a number of advantages with respect to monoclonals. By binding to multiple sites on a target, polyclonal antibodies or other polypeptides can generate a stronger signal (for diagnostics) or greater blocking/inhibition/cytotoxicity (for therapeutics) than a monoclonal that binds to a single site. Further, a polyclonal preparation can bind to numerous variants of a prototypical target sequence (e.g., allelic variants, species variants, strain variants, drug-induced escape variants) whereas a monoclonal antibody may bind only to the prototypical sequence or a narrower range of variants thereto.

Polyclonal preparations of antibodies and other polypeptides can be incorporated into compositions for diagnostic or therapeutic use. The preferred form depends on the intended mode of administration and diagnostic or therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like. See *Remington's Pharmaceutical Science,* (15th ed., Mack Publishing Company, Easton, Pa., 1980). Compositions intended for in vivo use are usually sterile.

Although the invention has been described in detail for purposes of clarity of understanding, it will be obvious that certain modifications may be practiced within the scope of the appended claims. All publications and patent documents cited in this application are hereby incorporated by reference in their entirety for all purposes to the same extent as if each were so individually denoted. Cell lines producing antibodies designated 7F11, CD43.5.PC, CD43.9, CDTXA1.PC, referred to in the following examples, have been deposited with the American Type Culture Collection, on Apr. 3 and Dec. 5, 1997 under the Budapest Treaty and given the Accession Nos. HB12443, 98389, 98390, and 98388, respectively. These deposit will be maintained at an authorized depository and replaced in the event of mutation, nonviability or destruction for a period of at least five years after the most recent request for release of a sample was received by the depository, for a period of at least thirty years after the date of the deposit, or during the enforceable life of the related patent, whichever period is longest. All restrictions on the availability to the public of these cell lines will be irrevocably removed upon the issuance of a patent from the application.

EXAMPLES

Example 1

Immunization of Mice with Antigens and Purification of RNA from Mouse Spleens

Mice were immunized by the following method based on experience of the timing of spleen harvest for optimal recovery of mRNA coding for antibody. Two species of mice were used: Balb/c (Charles River Laboratories, Wilmington, Mass.) and A/J (Jackson Laboratories, Bar Harbor, Me.). Each of ten mice were immunized intraperitoneally with antigen using 50 μg protein in Freund's complete adjuvant on day 0, and day 28. Tests bleeds of mice were obtained through puncture of the retro-orbital sinus. If, by testing the titers, they were deemed high by ELISA using biotinylated antigen immobilized via streptavidin, the mice were boosted with 50 μg of protein on day 70, 71 and 72, with subsequent sacrifice and splenectomy on day 77. If titers of antibody were not deemed satisfactory, mice were boosted with 50 μg antigen on day 56 and a test bleed taken on day 63. If satisfactory titers were obtained, the animals were boosted with 50 μg of antigen on day 98, 99, and 100 and the spleens harvested on day 105. Typically, a test bleed dilution of 1:3200 or more resulted in a half maximal ELISA response to be considered satisfactory.

The spleens were harvested in a laminar flow hood and transferred to a petri dish, trimming off and discarding fat and connective tissue. The spleen was, working quickly, macerated with the plunger from a sterile 5 cc syringe in the presence of 1.0 ml of solution D (25.0 g guanidine thiocyanate (Boehringer Mannheim, Indianapolis, Ind.), 29.3 ml sterile water, 1.76 ml 0.75 M sodium citrate (pH 7.0), 2.64 ml 10% sarkosyl (Fisher Scientific, Pittsburgh, Pa.), 0.36 ml 2-mercaptoethanol (Fisher Scientific, Pittsburgh, Pa.)). The spleen suspension was pulled through an 18 gauge needle until viscous and all cells were lysed, then transferred to a microcentrifuge tube. The petri dish was washed with 100 μl of solution D to recover any remaining spleen, and this was transferred to the tube. The suspension was then pulled through a 22 gauge needle an additional 5–10 times. The sample was divided evenly between two microcentrifuge tubes and the following added in order, with mixing by inversion after each addition: 100 μl 2 M sodium acetate (pH 4.0), 1.0 ml water-saturated phenol (Fisher Scientific, Pittsburgh, Pa.), 200 μl chloroform/isoamyl alcohol 49:1 (Fisher Scientific, Pittsburgh, Pa.). The solution was vortexed for 10 seconds and incubated on ice for 15 min. Following centrifugation at 14 krpm for 20 min at 2–8° C., the aqueous phase was transferred to a fresh tube. An equal volume of water saturated phenol/chloroform/isoamyl alcohol (50:49:1) was added, and the tube was vortexed for ten seconds. After a 15 min incubation on ice, the sample was centrifuged for 20 min at 2–8° C., and the aqueous phase was transferred to a fresh tube and precipitated with an equal volume of isopropanol at −20° C. for a minimum of 30 min. Following centrifugation at 14 krpm for 20 min at 4° C., the supernatant was aspirated away, the tubes briefly spun and all traces of liquid removed. The RNA pellets were each dissolved in 300 μl of solution D, combined, and precipitated with an equal volume of isopropanol at −20° C. for a minimum of 30 min. The sample was centrifuged 14 krpm for 20 min at 4° C., the supernatant aspirated as before, and the sample rinsed with 100 μl of ice-cold 70% ethanol. The sample was again centrifuged 14 krpm for 20 min at 4° C., the 70% ethanol solution aspirated, and the RNA pellet dried in vacuo. The pellet was resuspended in 100 μl of sterile distilled water. The concentration was determined by $A_{260}$ using an absorbance of 1.0 for a concentration of 40 μg/ml. The RNA was stored at −80° C.

Example 2
Preparation of Complementary DNA (cDNA)

The total RNA purified as described above was used directly as template for cDNA. RNA (50 μg) was diluted to 100 μL with sterile water, and 10 μL–130 ng/μL oligo $dT_{12}$ (synthesized on Applied Biosystems Model 392 DNA synthesizer at Biosite Diagnostics) was added. The sample was heated for 10 min at 70° C., then cooled on ice. 40 μL 5×first strand buffer was added (Gibco/BRL, Gaithersburg, Md.), 20 μL 0.1 M dithiothreitol (Gibco/BRL, Gaithersburg, Md.), 10 μL 20 mM deoxynucleoside triphosphates (dNTP's, Boehringer Mannheim, Indianapolis, Ind.), and 10 μL water on ice. The sample was then incubated at 37° C. for 2 min. 10 μL reverse transcriptase (Superscript™ II, Gibco/BRL, Gaithersburg, Md.) was added and incubation was continued at 37° C. for 1 hr. The cDNA products were used directly for polymerase chain reaction (PCR).

Example 3
Amplification of cDNA by PCR

To amplify substantially all of the H and L chain genes using PCR, primers were chosen that corresponded to substantially all published sequences. Because the nucleotide sequences of the amino terminals of H and I contain considerable diversity, 33 oligonucleotides were synthesized to serve as 5' primers for the H chains (FIG. 1), and 29 oligonucleotides were synthesized to serve as 5' primers for the kappa L chains (FIG. 2). The 5' primers were made according to the following criteria. First, the second and fourth amino acids of the L chain and the second amino acid of the heavy chain were conserved. Mismatches that changed the amino acid sequence of the antibody were allowed in any other position. Second, a 20 nucleotide sequence complementary to the M13 uracil template was synthesized on the 5' side of each primer. This sequence is different between the H and L chain primers, corresponding to 20 nucleotides on the 3' side of the pelB signal sequence for L chain primers and the alkaline phosphatase signal sequence for H chain primers. The constant region nucleotide sequences required only one 3' primer each to the H chains and the kappa L chains (FIG. 2). Amplification by PCR was performed separately for each pair of 5' and 3' primers. A 50 μL reaction was performed for each primer pair with 50 pmol of 5' primer, 50 pmol of 3' primer, 0.25 μL Taq DNA Polymerase (5 units/μL, Boehringer Mannheim, Indianapolis, Ind.), 3 μL cDNA (described in Example 2), 5 μL 2 mM dNTP's, 5 μL 10×Taq DNA polymerase buffer with $MgCl_2$ (Boehringer Mannheim, Indianapolis, Ind.), and $H_2O$ to 50 μL. Amplification was done using a GeneAmp® 9600 thermal cycler (Perkin Elmer, Foster City, Calif.) with the following program: 94° C. for 1 min; 30 cycles of 94° C. for 20 sec, 55° C. for 30 sec, and 72° C. for 30 sec; 72° C. for 6 min; 4° C.

The dsDNA products of the PCR process were then subjected to asymmetric PCR using only 3' primer to generate substantially only the anti-sense strand of the target genes. A 100 μL reaction was done for each dsDNA product with 200 pmol of 3' primer, 2 μL of ds-DNA product, 0.5 μL Taq DNA Polymerase, 10 μL 2 mM dNTP's, 10 μL 10×Taq DNA polymerase buffer with $MgCl_2$ (Boehringer Mannheim, Indianapolis, Ind.), and $H_2O$ to 100 μL. The same PCR program as that described above was used to amplify the single-stranded (ss)-DNA.

Example 4
Purification of ss-DNA by High Performance Liquid Chromatography and Kinasing ss-DNA The H chain ss-PCR products and the L chain ss-PCR products were ethanol precipitated by adding 2.5 volumes ethanol and 0.2 volumes 7.5 M ammonium acetate and incubating at −20° C. for at least 30 min. The DNA was pelleted by centrifuging in an Eppendorf centrifuge at 14 krpm for 10 min at 2–8° C. The supernatant was carefully aspirated, and the tubes were briefly spun a 2nd time. The last drop of supernatant was removed with a pipet. The DNA was dried in vacuo for 10 min on medium heat. The H chain products were pooled in 210 μL water and the L chain products were pooled separately in 210 μL water. The ss-DNA was purified by high performance liquid chromatography (HPLC) using a Hewlett Packard 1090 HPLC and a Gen-Pak™ FAX anion exchange column (Millipore Corp., Milford, Mass.). The gradient used to purify the ss-DNA is shown in Table 1, and the oven temperature was at 60° C. Absorbance was monitored at 260 nm. The ss-DNA eluted from the HPLC was collected in 0.5 min fractions. Fractions containing ss-DNA were ethanol precipitated, pelleted and dried as described above. The dried DNA pellets were pooled in 200 μL sterile water.

TABLE 1

HPLC gradient for purification of ss-DNA

| Time (min) | % A | % B | % C | Flow (mL/min) |
|---|---|---|---|---|
| 0 | 70 | 30 | 0 | 0.75 |
| 2 | 40 | 60 | 0 | 0.75 |
| 32 | 15 | 85 | 0 | 0.75 |
| 35 | 0 | 100 | 0 | 0.75 |
| 40 | 0 | 100 | 0 | 0.75 |
| 41 | 0 | 0 | 100 | 0.75 |
| 45 | 0 | 0 | 100 | 0.75 |
| 46 | 0 | 100 | 0 | 0.75 |
| 51 | 0 | 100 | 0 | 0.75 |
| 52 | 70 | 30 | 0 | 0.75 |

Buffer A is 25 mM Tris, 1 mM EDTA, pH 8.0
Buffer B is 25 mM Tris, 1 mM EDTA, 1 M NaCl, pH 8.9
Buffer C is 40 mm phosphoric acid The ss-DNA was kinased on the 5' end in preparation for mutagenesis (Example 7). 24 μL 10×kinase buffer (United States Biochemical, Cleveland, Ohio), 10.4 μl 10 mM adenosine-5'-triphosphate (Boehringer Mannheim, Indianapolis, Ind.), and 2 μL polynucleotide kinase (30 units/μL, United States Biochemical, Cleveland, Ohio) was added to each sample, and the tubes were incubated at 37° C. for 1 hr. The reactions were stopped by incubating the tubes at 70° C. for 10 min. The DNA was purified with one extraction of equilibrated phenol (pH>8.0, United States Biochemical, Cleveland, Ohio)-chloroformisoamyl alcohol (50:49:1) and one extraction with chloroform:isoamyl alcohol (49:1). After the extractions, the DNA was ethanol precipitated and pelleted as described above. The DNA pellets were dried, then dissolved in 50 μL sterile water. The concentration was determined by measuring the absorbance of an aliquot of the DNA at 260 nm using 33 μg/mL for an absorbance of 1.0. Samples were stored at −20° C.

Example 5
Antibody Phage Display Vector

The antibody phage display vector for cloning antibodies was derived from an M13 vector supplied by Ixsys, designated 668-4. The vector 668-4 contained the DNA sequences encoding the heavy and light chains of a mouse monoclonal Fab fragment inserted into a vector described by Huse, WO 92/06024. The vector had a Lac promoter, a pelB signal sequence fused to the 5' side of the L chain variable region of the mouse antibody, the entire kappa chain of the mouse antibody, an alkaline phosphatase signal sequence at the 5' end of the H chain variable region of the mouse antibody, the entire variable region and the first constant region of the H chain, and 5 codons of the hinge region of an IgG1 H chain. A decapeptide sequence was at the 3' end of the H chain hinge region and an amber stop codon separated the decapeptide sequence from the pseudo-gene VIII sequence. The amber stop allowed expression of H chain fusion proteins with the gene VIII protein in *E. coli* suppressor strains such as XL1 blue (Stratagene, San Diego, Calif.), but not in nonsuppressor cell strains such as MK30 (Boehringer Mannheim, Indianapolis, Ind.) (see FIG. 3A).

To make the first derivative cloning vector, deletions were made in the variable regions of the H chain and the L chain by oligonucleotide directed mutagenesis of a uracil template (Kunkel, *Proc. Natl. Acad. Sci. USA* 82, 488 (1985); Kunkel et al., *Methods. Enzymol.* 154, 367 (1987)). These mutations deleted the region of each chain from the 5' end of CDR1 to the 3' end of CDR3, and the mutations added a DNA sequence where protein translation would stop (see FIG. 4 for mutagenesis oligonucleotides). This prevented the expression of H or L chain constant regions in clones without an insert, thereby allowing plaques to be screened for the presence of insert. The resulting cloning vector was called BS11.

Many changes were made to BS11 to generate the cloning vector used in the present screening methods. The amber stop codon between the heavy chain and the pseudo gene VIII sequence was removed so that every heavy chain was expressed as a fusion protein with the gene VIII protein. This increased the copy number of the antibodies on the phage relative to BS11. A HindIII restriction enzyme site in the sequence between the 3' end of the L chain and the 5' end of the alkaline phosphatase signal sequence was deleted so antibodies could be subcloned into a pBR322 derivative (Example 13). The interchain cysteine residues at the carboxy-terminus of the L and H chains were changed to serine residues. This increased the level of expression of the antibodies and the copy number of the antibodies on the phage without affecting antibody stability. Nonessential DNA sequences on the 5' side of the lac promoter and on the 3'side of the pseudo gene VIII sequence were deleted to reduce the size of the M13 vector and the potential for rearrangement. A transcriptional stop DNA sequence was added to the vector at the L chain cloning site to replace the translational stop so that phage with only heavy chain proteins on their surface, which might be nonspecifically in panning, could not be made. Finally, DNA sequences for protein tags were added to different vectors to allow enrichment for polyvalent phage by metal chelate chromatography (polyhistidine sequence) or by affinity purification using a decapeptide tag and a magnetic latex having an immobilized antibody that binds the decapeptide tag. The vector BS39 had a polyhistidine sequence at the 3' end of the kappa chain with no tag at the end of the heavy chain (FIG. 3B) BS45 had a polyhistidine sequence between the end of the heavy chain constant region and the pseudo-gene VIII sequence, and a decapeptide sequence at the 3' end of the kappa chain constant region (FIG. 3C).

Example 6
Preparation of Uracil Templates used in Generation of Spleen Antibody Phase Libraries 1 mL of *E. coli* CJ236 (BioRAD, Hercules, Calif.) overnight culture was added to 50 ml 2×YT in a 250 mL baffled shake flask. The culture was grown at 37° C. to $OD_{600}$=0.6, inoculated with 10 μl of a 1/100 dilution of vector phage stock and growth continued for 6 hr. Approximately 40 mL of the culture was centrifuged at 12 krpm for 15 minutes at 4° C. The supernatant (30 mL) was transferred to a fresh centrifuge tube and incubated at room temperature for 15 minutes after the addition of 15 μl of 10 mg/ml RnaseA (Boehringer Mannheim, Indianapolis, Ind.). The phage were precipitated by the addition of 7.5 ml of 20% polyethylene glycol 8000 (Fisher Scientific, Pittsburgh, Pa.)/3.5M ammonium acetate (Sigma Chemical Co., St. Louis, Mo.) and incubation on ice for 30 min. The sample was centrifuged at 12 krpm for 15 min at 2–8° C. The supernatant was carefully discarded, and the tube was briefly spun to remove all traces of supernatant. The pellet was resuspended in 400 μl of high salt buffer (300 mM NaCl, 100 mM Tris pH 8.0, 1 mM EDTA), and transferred to a 1.5 mL tube. The phage stock was extracted repeatedly with an equal volume of equilibrated phenol:chloroform:isoamyl alcohol (50:49:1) until no trace of a white interface was visible, and then extracted with an equal volume of chloroform:isoamyl alcohol (49:1). The DNA was precipitated with 2.5 volumes of ethanol and 1/5 volume 7.5 M ammonium acetate and incubated 30 min at −20° C. The DNA was centrifuged at 14 krpm for 10 min at 4° C., the pellet washed once with cold 70% ethanol, and dried in vacuo. The uracil template DNA was dissolved in 30 μl sterile water and the concentration determined by $A_{260}$ using an absorbance of 1.0 for a concentration of 40 μg/ml. The template was diluted to 250 ng/μl with sterile water, aliquoted, and stored at −20° C.

Example 7
Mutagenesis of Uracil Template with ss-DNA and Electroporation into *E. coli* to Generate Antibody Phase Libraries Antibody phage-display libraries were generated by simultaneously introducing single-stranded heavy and light chain genes onto a phage-display vector uracil template. A typical mutagenesis was performed on a 2 μg scale by mixing the following in a 0.2 mL PCR reaction tube: 8 μl of (250 ng/μl) uracil template (examples 5 and 6), 8 μl of 10×annealing buffer (200 mM Tris pH 7.0, 20 mM $MgCl_2$, 500 mM NaCl), 3.33 μl of kinased single-stranded heavy chain insert (100 ng/μl), 3.1 μl of kinased single-stranded light chain insert (100 ng/ml), and sterile water to 80 μl. DNA was annealed in a GeneAmp® 9600 thermal cycler using the following thermal profile: 20 sec at 94° C., 85° C. for 60 sec, 85° C. to 55° C. ramp over 30 min, hold at 55° C. for 15 min. The DNA was transferred to ice after the program finished. The extension/ligation was carried out by adding 8 μl of 10×synthesis buffer (5 mM each dNTP, 10 mM ATP, 100 mM Tris pH 7.4, 50 mM $MgCl_2$, 20 mM DTT), 8 μl T4 DNA ligase (1 U/μl, Boehringer Mannheim, Indianapolis, Ind.), 8 μl diluted T7 DNA polymerase (1 U/μl, New England BioLabs, Beverly, Mass.) and incubating at 37° C. for 30 min. The reaction was stopped with 300 μl of mutagenesis stop buffer (10 mM Tris pH 8.0, 10 mM EDTA). The mutagenesis DNA was extracted once with equilibrated phenol (pH>8):chloroform:isoamyl alcohol (50:49:1), once with chloroform:isoamyl alcohol (49:1), and the DNA was ethanol precipitated at −20° C. for at least 30 min. The DNA was pelleted and the supernatant carefully removed as described above. The sample was briefly spun again and all traces of ethanol removed with a pipetman. The pellet was dried in vacuo. The DNA was resuspended in 4 μl of sterile water. 1 μl mutagenesis DNA was (500 ng) was transferred into 40 μl electrocompetent *E. coli* DH12S (Gibco/BRL, Gaithersburg, Md.) using the electroporation conditions in Example 8. The transformed cells were mixed with 1.0 mL 2×YT broth (Sambrooke et al., supra) and transferred to 15 mL sterile culture tubes. The first round antibody phage was made by shaking the cultures overnight at 23° C. and 300 rpm. The efficiency of the electroporation was measured by plating 10 μl of $10^{-3}$ and $10^{-4}$ dilutions of the cultures on LB agar plates (see Example 12). These plates were incubated overnight at 37° C. The efficiency was determined by multiplying the number of plaques on the $10^{-3}$ dilution plate by $10^5$ or multiplying the number of plaques on the $10^{-4}$ dilution plate by $10^6$. The overnight cultures from the electroporations were transferred to 1.5 ml tubes, and the cells were pelleted by centrifuging at 14 krpm for 5 min. The supernatant, which is the first round of antibody phage, was then transferred to 15 mL sterile centrifuge tubes with plug seal caps.

Example 8
Transformation of E. coli by Electroporation

The electrocompetent E. coli cells were thawed on ice. DNA was mixed with 20–40 μL electrocompetant cells by gently pipetting the cells up and down 2–3 times, being careful not to introduce air-bubble. The cells were transferred to a Gene Pulser cuvette (0.2 cm gap, BioRAD, Hercules, Calif.) that had been cooled on ice, again being careful not to introduce an air-bubble in the transfer. The cuvette was placed in the E. coli Pulser (BioRAD, Hercules, Calif.) and electroporated with the voltage set at 1.88 kV according to the manufacturer's recommendation. The transformed sample was immediately diluted to 1 ml with 2xYT broth and processed as procedures dictate.

Example 9
Preparation of Biotinylated Antigens and Antibodies

Protein antigens or antibodies were dialyzed against a minimum of 100 volumes of 20 mM borate, 150 mM NaCl, pH 8 (BBS) at 2–8° C. for at least 4 hr. The buffer was changed at least once prior to biotinylation. Protein antigens or antibodies were reacted with biotin-XX-NHS ester (Molecular Probes, Eugene, Oreg., stock solution at 40 mM in dimethylformamide) at a final concentration of 1 mM for 1 hr at room temperature. After 1 hr, the protein antigens or antibodies were extensively dialyzed into BBS to remove unreacted small molecules.

Example 10
Preparation of Alkaline Phosphatase-Antigen Conjugates

Alkaline phosphatase (AP, Calzyme Laboratories, San Luis Obispo, Calif.) was placed into dialysis versus a minimum of 100 volumes of column buffer (50 mM potassium phosphate, 10 mM borate, 150 mM NaCl, 1 mM $MgSO_4$, pH 7.0) at 2–8° C. for at least four hr. The buffer was changed at least twice prior to use of the AP. When the AP was removed from dialysis and brought to room temperature, the concentration was determined by absorbance at 280 nm using an absorbance of 0.77 for a 1 mg/mL solution. The AP was diluted to 5 mg/mL with column buffer. The reaction of AP and succinimidyl 4-(N-maleimidomethyl)cyclohexane-1-carboxylate (SMCC, Pierce Chemical Co., Rockford, Ill.) was carried out using a 20:1 ratio of SMCC:AP. SMCC was dissolved in acetonitrile at 20 mg/mL and diluted by a factor of 84 when added to AP while vortexing or rapidly stirring. The solution was allowed to stand at room temperature for 90 min before the unreacted SMCC and low molecular weight reaction products were separated from the AP using gel filtration chromatography (G50 Fine, Pharmacia Biotech, Piscataway, N.J.) in a column equilibrated with column buffer.

Protein antigen was dialyzed versus a minimum of 100 volumes of 20 mM potassium phosphate, 4 mM borate, 150 mM NaCl, pH 7.0 at 2–8° C. for at least four hr. The buffer was changed at least twice prior to use of the antigen. The amount of antigen was quantitated by absorbance at 280 nm. The extinction coefficient for creatine kinase MB subunits (CKMB, Scripps Laboratories, San Diego, Calif.) was 0.88 mL/mg-cm, Clostridium difficile toxin A (Tech Lab, Blacksburg, Va.) was 1.29 mL/mg-cm, and Clostridium difficile glutamate dehydrogenase (Example 19) was 1.45 mL/mg-cm. The reaction of antigen and N-succinimidyl 3-[2-pyridyldithio]propionate (SPDP, Pierce Chemical Co., Rockford, Ill.) was carried out using a 20:1 molar ratio of SPDP:antigen. SPDP was dissolved in dimethylformamide at 40 mM and diluted into the antigen solution while vortexing. The solution was allowed to stand at room temperature for 90 min, at which time the reaction was quenched by adding taurine (Aldrich Chemical Co., Milwaukee, Wis.) to a final concentration of 20 mM for 5 min. Dithiothreitol (Fisher Scientific, Pittsburgh, Pa.) was added to the protein at a final concentration of 1 mM for 30 min. The low molecular weight reaction products were separated from the antigen using gel filtration chromatography in a column equilibrated in 50 mM potassium phosphate, 10 mM borate, 150 mM NaCl, 0.1 mM ethylene diamine tetraacetic acid (EDTA, Fisher Scientific, Pittsburgh, Pa.), pH 7.0.

The AP and antigen were mixed together in an equimolar ratio. The reaction was allowed to proceed at room temperature for 2 hr. The conjugate was diluted to 0.1 mg/mL with block containing 1% bovine serum albumin (from 30% BSA, Bayer, Kankakee, Ill.), 10 mM Tris, 150 mM NaCl, 1 mM $MgCl_2$, 0.1 mM $ZnCl_2$, 0.1% polyvinyl alcohol (80% hydrolyzed, Aldrich Chemical Co., Milwaukee, Wis.), pH 8.0.

Example 11
Preparation of Avidin Magnetic Latex

The magnetic latex (Estapor, 10% solids, Bangs Laboratories, Fishers, Ind.) was thoroughly resuspended and 2 ml aliquoted into a 15 ml conical tube. The magnetic latex was suspended in 12 ml distilled water and separated from the solution for 10 min using a magnet. While still in the magnet, the liquid was carefully removed with a 10 mL sterile pipet. This washing process was repeated an additional three times. After the final wash, the latex was resuspended in 2 ml of distilled water. In a separate 50 ml conical tube, 10 mg of avidin-HS (NeutrAvidin, Pierce, Rockford, Ill.) was dissolved in 18 ml of 40 mM Tris, 0.15 M sodium chloride, pH 7.5 (TBS). While vortexing, the 2 ml of washed magnetic latex was added to the diluted avidin-HS and the mixture vortexed an additional 30 seconds. This mixture was incubated at 45° C. for 2 hr, shaking every 30 minutes. The avidin magnetic latex was separated from the solution using a magnet and washed three times with 20 ml BBS as described above. After the final wash, the latex was resuspended in 10 ml BBS and stored at 4° C.

Immediately prior to use, the avidin magnetic latex was equilibrated in panning buffer (40 mM TRIS, 150 mM NaCl, 20 mg/mL BSA, 0.1% Tween 20 (Fisher Scientific, Pittsburgh, Pa.), pH 7.5). The avidin magnetic latex needed for a panning experiment (200 μl/sample) was added to a sterile 15 ml centrifuge tube and brought to 10 ml with panning buffer. The tube was placed on the magnet for 10 min to separate the latex. The solution was carefully removed with a 10 mL sterile pipet as described above. The magnetic latex was resuspended in 10 mL of panning buffer to begin the second wash. The magnetic latex was washed a total of 3 times with panning buffer. After the final wash, the latex was resuspended in panning buffer to the initial aliquot volume.

Example 12
Plating M13 Phage or Cells Transformed with Antibody Phage-Display Vector Mutagenesis Reaction The phage samples were added to 200 µL of an overnight culture of *E. coli* XL1-Blue when plating on 100 mm LB agar plates or to 600 µL of overnight cells when plating on 150 mm plates in sterile 15 ml culture tubes. After adding LB top agar (3 mL for 100 mm plates or 9 mL for 150 mm plates, top agar stored at 55° C., Appendix A1, Molecular Cloning, A Laboratory Manual, (1989) Sambrook. J), the mixture was evenly distributed on an LB agar plate that had been pre-warmed (37° C.–55° C.) to remove any excess moisture on the agar surface. The plates were cooled at room temperature until the top agar solidified. The plates were inverted and incubated at 37° C. as indicated.

Example 13
Develop Nitrocellulose Filters with Alkaline Phosphatase Conjugates After overnight incubation of the nitrocellulose filters on LB agar plates, the filters were carefully removed from the plates with membrane forceps and incubated for 2 hr in either casein block (block with 1% casein (Hammersten grade, Research Organics, Cleveland, Ohio)), when using antigen-AP conjugates or block when using goat anti-mouse kappa-AP (Southern Biotechnology Associates, Inc, Birmingham, Ala.). After 2 hr, the filters were incubated with the AP conjugate for 2–4 hr. Antigen-AP conjugates were diluted into casein block at a final concentration of 1 µg/mL and goat anti-mouse kappa-AP conjugates were diluted into block at a final concentration of 1 µg/mL. Filters were washed 3 times with 40 mM TRIS, 150 mM NaCl, 0.05% Tween 20, pH 7.5 (TBST) (Fisher Chemical, Pittsburgh, Pa.) for 5 min each. After the final wash, the filters were developed in a solution containing 0.2 M 2-amino-2-methyl-1-propanol (JBL Scientific, San Luis Obispo, Calif.), 0.5 M TRIS, 0.33 mg/mL nitro blue tetrazolium (Fisher Scientific, Pittsburgh, Pa.) and 0.166 mg/mL 5-bromo-4-chloro-3-indolyl-phosphate, p-toluidine salt.

Example 14
Enrichment of Polyclonal Phage to CKMB with No Tags on the Heavy Chain and a Polyhistidine Sequence on the Kappa Chain This example describes multiple rounds of screening of a phage library to the antigen creatine kinase MB (M and B designate muscle and brain subunits). Some of the rounds of screening to CKMB were alternated with rounds of enrichment for phage displaying multiple copies of antibodies. The percentage of phage displaying any light chain, and the percentage of phage displaying Fab fragments with specific affinity for CKMB was measured after each round of screening to CKMB.

The first round antibody phage was prepared as described above using BS39 uracil template. Two electroporations of mutagenesis DNA had efficiencies of $9.7 \times 10^7$ PFU and $8.3 \times 10^7$ PFU. The phage from both electroporations were combined and diluted to 3.2 with panning buffer. The phage was aliquoted into 2–1 mL aliquots in 15 mL disposable sterile centrifuge tubes with plug seal caps. CKMB-biotin (10 µL, $10^{-6}$ M stock concentration) was added to each phage aliquot. The phage samples were incubated overnight at 2–8° C. After the incubation, the phage samples were panned with avidin magnetic latex. The equilibrated avidin magnetic latex (see Example 11), 200 µL latex per sample, was incubated with the phage for 10 min at room temperature. After 10 min, approximately 9 mL of panning buffer was added to each phage sample, and the magnetic latex was separated from the solution using a magnet. After 10 min in the magnet, the unbound phage was carefully removed with a 10 mL sterile pipet. The magnetic latex was then resuspended in 10 mL of panning buffer to begin the second wash. The latex was washed a total of 5 times as described above. For each wash, the tubes were in the magnet for 10 min to separate unbound phage from the magnetic latex. After the 5th wash, the magnetic latex was resuspended in 1 mL TBS and transferred to a 1.5 mL tube. Aliquots of the latex were taken at this point to plate on 100 mm LB agar plates as described above. The bulk of the magnetic latex (99%) was resuspended in 200 µL 2×YT and was plated on a 150 mm LB agar plate as described in Example 12. The 100 mm LB agar plates were incubated at 37° C. for 6–7 hr, then the plates were transferred to room temperature and nitrocellulose filters (pore size 0.45 µm, BA85 Protran, Schleicher and Schuell, Keene, N.H.) were overlayed onto the plaques. Plates with nitrocellulose filters were incubated overnight at room temperature. The 150 mm plates were used to amplify the phage binding to the magnetic latex to generate the next round of antibody phage. These plates were incubated at 37° C. for 4 hr, then overnight at 20° C.

After the overnight incubation, the antibody phage was eluted from the 150 mm plates, and the filters were developed with alkaline phosphatase-CKMB as described in Example 13. The antibody phage was eluted from the 150 mm plates by pipeting 8 mL 2YT media onto the lawn and gently shaking the plate at room temperature for 20 min. The phage were transferred to a 15 mL disposable sterile centrifuge tubes with plug seal cap and the debris from the LB plate was pelleted by centrifuging for 15 min at 3500 rpm. The 2nd round antibody phage was then transferred to a new tube.

To begin the 2nd round of panning, the antibody phage were titered by plating 10 µL of $10^{-7}$ and $10^{-8}$ dilutions of the phage on 100 mm LB agar plates. The plates were incubated at 37° C. for 6–7 hr, then the number of plaques on the plates were counted. Also, to monitor the percentage of kappa positives in the antibody phage, a nitrocellulose filter was overlayed onto the plate and incubated overnight at room temperature. The percentage of kappa positives is a measure of the proportion of phage displaying intact Fab fragments.

Both 2nd round antibody phage samples were pooled by diluting each sample into panning buffer at a final concentration of $5 \times 10^9$ PFU/mL to a final volume of 1 mL. (The titers of the antibody phage were about $2 \times 10^{12}$ PFU/mL and $1.7 \times 10^{12}$). CKMB-biotin (10 µL, $10^{-6}$ M stock concentration) was added to the phage and the phage was incubated at 2–8° C. overnight. The nitrocellulose filters on the antibody phage titer plates were developed with goat anti-mouse kappa AP as described in Example 13. The second round antibody phage was panned with avidin magnetic latex as described above. After washing the latex with panning buffer, the latex was resuspended in 1 mL TBS and transferred to a 1.5 mL tube. Aliquots of the latex were plated on 100 mm LB agar plates as described above to check functional positives, and the rest of the latex was plated on 150 mm LB agar plates to generate the 3rd round antibody phage. This general procedure of titering the antibody phage, diluting the phage into panning buffer and adding CKMB-biotin, incubating the phage at least 16 hr at 2–8° C., panning the phage with avidin magnetic latex, and plating the magnetic latex was followed through 10 rounds of panning. The only changes from that described above is the concentration of CKMB-biotin was lower to increase the affinity of bound antibodies, and the number of phage panned was between $10^{10}$ and $10^8$. The results of the filter lifts on the percentage of kappa positives in the antibody phage and the percentage of functional antibodies binding to the magnetic latex are shown in Table 2.

After the 10th round of panning to CKMB-biotin, the antibody phage were subject to a round of enrichment for polyvalent display. Enrichment was effected by binding of the hexahistidine tag fused to the displayed light chain to NiNTA agarose (Qiagen Inc., Chatsworth, Calif.). The 11th round antibody phage (2.5 mL) were diluted into 2.5 mL panning buffer in a 15 mL disposable sterile centrifuge tube with plug seal cap. The NiNTA was equilibrated into panning buffer using the following procedure. The resin (1 mL per phage sample) was diluted to 50 mL with panning buffer in a 50 mL disposable sterile centrifuge tube with plug seal cap and then was pelleted in an IEC centrifuge at 500 rpm for 1 min. The supernatant was carefully removed with a 50 mL disposable pipet, then the resin was again diluted to 50 mL with panning buffer for the second wash. The resin was washed in this manner a total of 4 times in order to equilibrate the resin in panning buffer. The equilibrated resin was then resuspended to its original volume with panning buffer. Equilibrated resin (1 mL) was then added to the phage, and the tube was gently rocked for 15 min. After 15 min, the resin was pelleted in an IEC centrifuge at 500 rpm for 1 min. The supernatant was gently removed with a 10 mL disposable pipet, and the resin was resuspended in 10 mL panning buffer for the first wash. The resin was pelleted as described above, the supernatant was removed, and the resin was resuspended a 2nd time in 10 mL panning buffer. This procedure was repeated for a total of 5 panning buffer washes. After the 5th wash was removed, the resin was resuspended in 1 mL of elution buffer (50 mM citrate, 150 mM NaCl, pH 4.0) and transferred to a 1.5 mL tube. The resin was gently rocked for 1 hr to elute the antibody phage. After 1 hr, the resin was pelleted (14 krpm in Eppendorf centrifuge for 5 min), and the phage was removed while being careful not to transfer any resin. In order to adjust the pH of the phage solution to 8, 50 µL of 1 M Tris, pH 8.3 and 46 µL of 1 M NaOH were added to the 1 mL phage sample. Also, 10 µL of 300 mg/mL bovine serum albumin (Bayer, Kankakee, Ill.) was added to the phage sample. The resulting phage solution (1 mL) was transferred to a 15 mL disposable sterile centrifuge tube with plug seal cap for the 11th round of panning with CKMB-biotin, as described above. As shown in Table 2, panning the antibody phage with NiNTA prior to panning to CKMB significantly increased the percentage of CKMB functional positives binding to the avidin magnetic latex.

The 12th–14th rounds of panning were done as described above, where the antibody phage was bound to NiNTA, eluted, and the eluted phage panned with CKMB-biotin. However, in round 13, unlabelled creatine kinase BB subunits (Scripps Laboratories, San Diego, Calif.) and creatine kinase MM subunits (Scripps Laboratories, San Diego, Calif.) were added to the phage eluted from the NiNTA at 100-fold molar excess to the CKMB-biotin to select antibodies that specifically bind to CKMB without binding to CKMM or CKBB. The percentage of functional CKMB antibodies was greater than 95% by round 13.

TABLE 2

Summary of kappa positives and CKMB functional positives at each round of panning

| antibody phage % kappa | round # | phage binding to avidin latex % functional |
|---|---|---|
| 202/253 (80%) | 1 | 0/32 (0%) |
| 175/234 (75%) | 2 | 0/129 (0%) |
| 87/120 (73%) | 3 | 4/79 (5.1%) |
| 81/165 (49%) | 4 | 35/409 (8.6%) |
| 149/342 (44%) | 5 | 5/31 (16%) |
| 40/192 (21%) | 6 | 30/400 (7.5%) |
| 1/54 (2%) | 7 | 6/54 (11%) |
| 61/06 (6%) | 8 | 4/46 (9%) |
| 35/93 (38%) | 9 | 19/551 (3%) |
| 14/191 (7%) | 10 | 18/400 (5%) |
| N/A | 11 | 349/553 (53%) |
| 96/100 (96%) | 12 | 232/290 (80%) |
| 31/31 (100%) | 13 | (>95%) |
| 147/149 (99%) | 14 | 400/405 (99%) |

Table 2 illustrates the importance of polyvalent enrichment for making phage libraries with a high proportion of phage displaying antibodies with specific affinity for the chosen target (functional positives). The percentage of phage with specific affinity for the selected target is zero after the first two rounds of panning but then increase to about ten percent before levelling off in subsequent rounds of panning through round ten. Then in rounds 11–14, which are performed concurrently with polyvalent enrichment, the percentage of functional positive phage increases 99%. The rapid increase in functional positive phage in rounds 11–14, in which polyvalent enrichment is performed, compared with the plateau of about 10% achieved in rounds 1–10 without polyvalent enrichment illustrates the power of the present methods to achieve libraries with a high percent of functional positives.

The variation in percent kappa positives in different rounds of screening is also instructive. The percentage is initially high but decreases in the first ten rounds of screening (which are not performed concurrently with polyvalent enrichment). The decrease arises because kappa negative phage grow faster than kappa positive phage and are preferentially amplified between rounds of panning. In rounds 11–14, the percent of kappa positives increases to near 100%. The increase is due to polyvalent selection, which is effected by screening for phage displaying at least two kappa chains.

Example 15

Enrichment of Polyclonal Phage to *Clostridium difficile* Toxin A with a Polyhistidine Tag on the Heavy Chain; Selection of an Epitope Specificity on Toxin A Different from a Reference Antibody The first round antibody phage was prepared as described in Example 7 using BS45 uracil template. Eight electroporations of mutagenesis DNA were performed yielding 8 different phage samples. To create more diversity in the polyclonal library, each phage sample was panned separately. The antibody phage (about 0.9 mL) from each electroporation was transferred to a 15 mL disposable sterile centrifuge tube with plug seal cap. BSA (30 $\mu$L 300 mg/mL solution) and 1 M Tris (50 $\mu$L, 1 M stock solution, pH 8.0) were added to each phage stock, followed by 10 $\mu$L $10^{-6}$ M toxin A-biotin. The antibody phage was allowed to come to equilibrium with the toxin A-biotin by incubating the phage at 2–8° C. overnight. After the incubation, the phage were panned with avidin magnetic latex as described above in Example 14, except only 4 panning buffer washes were performed instead of 5. The entire magnetic latex of each sample was plated on 150 mm LB plates to generate the 2nd round antibody phage. The 150 mm plates were incubated at 37° C. for 4 hr, then overnight at 20° C.

The 2nd round antibody phage were eluted from the 150 mm plates as described in Example 14 except 10 mL 2×YT was used to elute the phage instead of 8 mL. The second round of panning was set up by diluting 100 µL of each phage stock (8 total) into 900 µL panning buffer in 15 mL disposable sterile centrifuge tubes with plug seal cap. Toxin A-biotin (10 µL of $10^{-7}$ M) was added to each sample, and the phage were incubated overnight at 2–8° C. The antibody phage were not titered before panning as described in Example 14. The phage samples were panned with avidin magnetic latex following the overnight incubation. After washing the latexes with panning buffer, each latex was plated on 150 mm LB agar plates. The plates were incubated at 37° C. for 4 hr, then 20° C. overnight.

The 3rd round antibody phage were bound to NiNTA resin and eluted prior to panning with toxin A-biotin. Each phage sample was bound to NiNTA and washed with panning buffer as described in Example 14. After the final wash, the antibody phage was eluted by adding 0.8 mL 300 mM imidazole (Fisher Scientific, Pittsburgh, Pa.) in panning buffear to each sample, and rocking the tubes for 10 min at room temperature. The resin was pelleted by centrifuging the tubes at 14 krpm for 5 min at room temperature, and the phage were carefully transferred to new tubes. Each phage sample was diluted to about 1.1 mL with panning buffer, then 1 mL of each sample was transferred to 15 mL disposable sterile centrifuge tube with plug seal cap. Toxin A-biotin (10 µL of $10^{-7}$M) was added to each sample, and the phage were incubated overnight at 2–8° C. After the overnight incubation, the phage were panned with avidin magnetic latex. After washing, each latex was resuspended in 1 mL panning buffer, and aliquots of each latex were plated on 100 mm LB agar plates to determine the percentage of kappa positives or functional positives. The majority of latex from each panning (99%) was plated on 150 mm LB agar plates to amplify the phage binding to the latex (see Example 14).

Two nitrocellulose filters from the 3rd round of panning were developed with goat anti-mouse kappa AP and had 83% and 85% positives. Six filters developed with toxin A-AP were all between 39–47% functional positive. At this point, 10 µL of $10^{-7}$ and 20 µL of $10^{-8}$ dilutions of each antibody phage stock were plated on 100 mm LB plates to determine the titers of each phage stock. The titers of the phage stocks were determined prior to pooling so that phage stocks with very high titers did not bias the antibody phage library. The titers (PFU/mL) were determined by counting the number of plaques on each plate and multiplying that number by $10^9$ ($10^{-7}$ dilution plate) or $5\times10^9$ ($10^{-8}$ dilution plate). Once the titers were determined, $2\times10^{11}$ PFU from each phage stock was pooled. The pooled phage (1.5 mL) was diluted to 5 mL with panning buffer, then the phage was panned with NiNTA. The eluted phage was panned to toxin A in the presence of an antibody to toxin A, PCG4 (described U.S. Pat. No. 4,533,630), to screen for phage-antibodies to toxin A that have a different specificity than PCG4. The eluted phage was diluted to about 1.1 mL with panning buffer, and 1 mL was aliquoted into a 15 mL tube. In a 1.5 mL tube, unlabeled toxin A (7.5 µL, $10^{-7}$M) and biotinylated PCG4 (15 µL, $10^{-6}$M) were mixed and incubated at room temperature for 15 min. A 20-fold molar excess of biotinylated antibody over toxin A was used so that no antibody phage could bind at the PCG4 epitope. The mixture of toxin A and biotinylated antibody (15 µL) was added to the 1 mL phage and incubated overnight at 2–80° C. The phage sample was panned with avidin magnetic latex as described in Example 14. The process of panning the eluted antibody phage, binding and eluting the phage with NiNTA, and panning the resulting eluted phage with biotinylated PCG4/toxin A was repeated 4 times. After the 5th round of selection, the polyclonal antibody phage stock complementary to PCG4 was 99% kappa positive and 98% had specific affinity for toxin A by plaque lift analysis.

Example 16

Enrichment of Polyclonal Phage to *Clostridium difficile* Glutamate Dehydrogenase Using a Decapeptide Tag on the Kappa Chain The first round antibody phage was prepared as described in Example 7 using BS45 uracil template, which has a hexahistidine tag for polyvalent enrichment fused to the heavy chain of displayed Fabs. Twelve electroporations of mutagenesis DNA from 4 different spleens (3 electroporations from each spleen) yielded 12 different phage samples. Each phage sample was panned separately to create more diversity in the polyclonal library. The antibody phage (about 0.9 mL) from each electroporation was transferred to a 15 mL disposable sterile centrifuge tube with plug seal cap. BSA (30 $\mu$L of a 300 mg/mL solution) and 1 M Tris (50 $\mu$L, pH 8.0) were added to each phage stock, followed by 10 $\mu$L $10^{-7}$ M glutamate dehydrogenase-biotin (Example 19). The antibody phage was allowed to come to equilibrium with the glutamate dehydrogenase-biotin by incubating the phage at room temperature for 4 hr. After the incubation, the phage samples were panned with avidin magnetic latex as described in Example 14. The entire latex of each sample was plated on 150 mm LB agar plates to generate the 2nd round antibody phage (Example 14). The resulting phage were panned with glutamate dehydrogenase-avidin-magnetic latex as described for the first round of panning.

A procedure was developed to enrich the antibody phage using the decapeptide tag on the kappa chain and a monoclonal antibody magnetic latex that binds the decapeptide. Binding studies had previously shown that the decapeptide could be eluted from the monoclonal antibody 7F11 (see Example 21) at a relatively mild pH of 10.5–11. The third round antibody phage resulting from panning NiNTA enriched 2nd round phage were bound to the 7F11 magnetic latex and eluted as described below. The 7F11 magnetic latex (2.5 mL) was equilibrated with panning buffer as described above for the avidin magnetic latex. Each phage stock (1 mL) was aliquoted into a 15 mL tube. The 7F11 magnetic latex (200 $\mu$L per phage sample) was incubated with phage for 10 min at room temperature. After 10 min, 9 mL of panning buffer was added, and the magnetic latex was separated from unbound phage by placing the tubes in a magnet for 10 min. The latexes were washed with 1 additional 10 mL panning buffer wash. Each latex was resuspended in 1 mL panning buffer and transferred to 1.5 mL tubes. The magnetic latex was separated from unbound phage by placing the tubes in a smaller magnet for 5 min, then the supernatant was carefully removed with a sterile pipet. Each latex was resuspended in 1 mL elution buffer (20 mM 3-(cyclohexylamino)propanesulfonic acid (United States Biochemical, Cleveland, Ohio), 150 mM NaCl, 20 mg/mL BSA, pH 10.5) and incubated at room temperature for 10 min. After 10 min, tubes were placed in the small magnet again for 5 min and the eluted phage was transferred to a new 1.5 mL tube. The phage samples were again placed in the magnet for 5 min to remove the last bit of latex that was transferred. Eluted phage was carefully removed into a new tube and 25 μL 3 M Tris, pH 6.8 was added to neutralize the phage. Panning with glutamate dehydrogenase-biotin was set up for each sample by mixing 900 μL 7F11/decapeptide enriched phage, 100 μL panning buffer, and 10 μL $10^{-7}$ M glutamate dehydrogenase-biotin and incubating overnight at 2–8° C. The phage was panned with avidin magnetic latex as described in Example 14.

One of the functional positive plaques was arbitrarily picked off an LB agar plate, and the antibody was subcloned into the expression vector described in Example 18. The monoclonal antibody was used as a reference to isolate polyclonal antibodies having different epitope specificity than the monoclonal antibody for sandwich assay development. This is similar to what is described above for toxin A except the monoclonal antibody for toxin A was a hybridoma antibody from a commercial source and the monoclonal antibody described here is from the antibody phage library.

The resulting 4th round antibody phage was panned again with 7F11 magnetic latex prior to functional panning. The eluted phage samples were set up for panning with the biotinylated monoclonal antibody (CD.43.9) and unlabelled glutamate dehydrogenase as described in Example 15 for toxin A antibodies. As discussed above, the monoclonal antibody was picked from the phage library and a polyclonal antibody phage stock that was complementary to the monoclonal was needed. Mixed the monoclonal antibody biotin (125 μL, $10^{-6}$M) and glutamate dehydrogenase (125 μL, $5\times10^{-8}$ M) at room temperature for 15 min. Added 20 μL of the mixture to each 1 mL phage sample (0.7 mL panning buffer and 0.3 mL phage eluted from the 7F11 latex), and incubated the samples overnight at 2–8° C. The phage samples were panned with the avidin magnetic latex following the standard procedure.

The 5th round antibody phage were eluted from the 150 mm LB agar plates as described in Example 15. The antibody phage were titered by plating 10 μL $10^{-7}$ dilutions of each phage stock on 100 mm LB agar plates. After 6 hr at 37° C., the number of plaques on each plate was counted, and the titers were calculated by multiplying the number of plaques by $10^9$. A pool of ten fifth round phage was made by mixing an equal number of phage from each phage stock so that high titer phage stocks would not bias the pool. Two of the samples were discarded because they had low functional percentages by plaque lift. The pooled phage were panned with 7F11 magnetic latex as described above. The eluted phage was set up for panning by mixing 0.1 mL panning buffer, 0.9 mL 7F11 eluted phage, and 20 μL monoclonal antibody biotin/glutamate dehydrogenase (see above). Phage were incubated overnight at 2–8° C. The phage sample was panned with avidin magnetic latex following the standard procedure. The phage binding to the latex was 97% functional positive by plaque lift assay.

Example 17
Construction of the pBR Expression Vector

Figure 7:
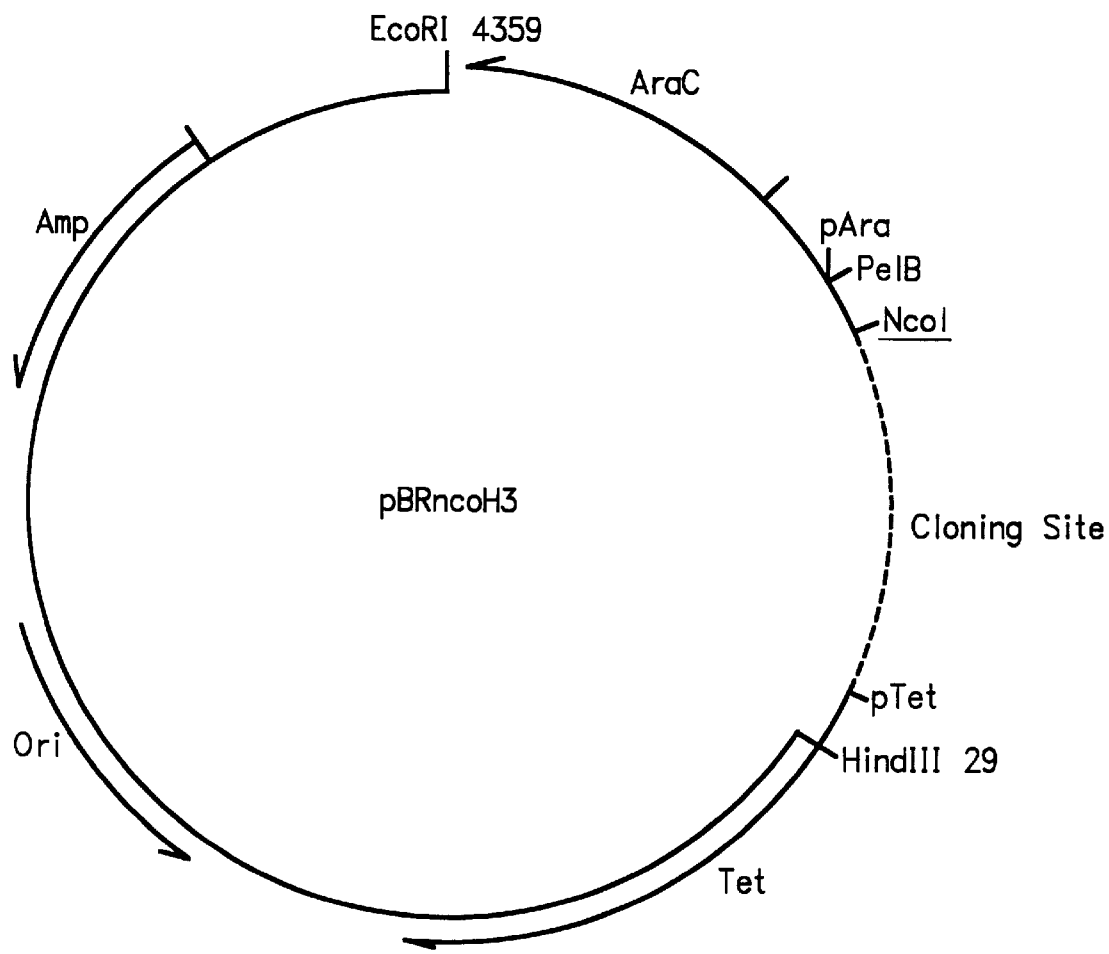
FIG. 7: Map of the vector pBRncoH3.

An expression vector and a process for the subcloning of monoclonal and polyclonal antibody genes from a phage-display vector has been developed that is efficient, does not substantially bias the polyclonal population, and can select for vector containing an insert capable of restoring antibiotic resistance. The vector is a modified pBR322 plasmid, designated pBRncoH3, that contains an arabinose promoter, ampicillin resistance (beta-lactamase) gene, a partial tetracycline resistance gene, a pelB (pectate lyase) signal sequence, and NcoI and HindIII restriction sites. (FIG. 7). The pBRncoH3 vector can also be used to clone proteins other than Fabs with a signal sequence. A second vector, pBRnsiH3, has been developed for cloning proteins with or without signal sequences, identical to the vector described above except that the pelB signal sequence is deleted and the NcoI restriction site has been replaced with an NsiI site.

The araC regulatory gene (including the araBAD promoter) as amplified from E. coli K-12 strain NL31-001 (a gift from Dr. Nancy Lee at UCSB) by PCR (Example 3) using Taq DNA polymerase (Boehringer Mannheim, Indianapolis, Ind.) with primers A and B (Table 3). Primers A and B contain 20 base-pairs of the BS39 vector sequence at their 5'-ends complementary to the 5' side of the lac promoter and the 5' side of the pelB signal sequence, respectively. Primer A includes an EcoRI restriction site at its 5'-end used later for ligating the ara insert into the pBR vector. The araCparaBAD PCR product was verified by agarose gel electrophoresis and used as template for an asymmetric PCR reaction with primer 'B' in order to generate the anti-sense strand of the insert. The single-stranded product was run on agarose gel electrophoresis, excised, purified with GeneClean (Bio101, San Diego, Calif.), and resuspended in water as per manufacturers recommendations. The insert was kinased with T4 polynucleotide kinase for 45 min at 37° C. The T4 polynucleotide kinase was heat inactivated at 70° C. for 10 min and the insert extracted with an equal volume of phenol/chloroform, followed by chloroform. The DNA was precipitated with ethanol at –20° C. for 30 min. The DNA was pelleted by centrifugation at 14 krpm for 15 min at 4° C., washed with ice-cold 70% ethanol, and dried in vacuo.

The insert was resuspended in water arid the concentration determined by $A_{260}$ using an absorbance of 1.0 for a concentration of 40 μg/ml. The insert was cloned into the phage-display vector BS39 for sequence verification and to introduce the pelB signal sequence in frame with the arabinose promoter (the pelB signal sequence also contains a NcoI restriction site at its 3'-end used later for ligating the ara insert into the pBR vector). The cloning was accomplished by mixing 250 ng of BS39 uracil template (Example 5), 150 ng of kinased araCpBAD insert, and 1.0 μl of 10×annealing buffer in a final volume of 10 μl. The sample was heated to 70° C. for 2 min and cooled over 20 min to room temperature to allow the insert and vector to anneal. The insert and vector were ligated together by adding 1 μl of 10×synthesis buffer, 1 μl T4 DNA ligase (1 U/μl), 1 μl T7 DNA polymerase (1 U/μl) and incubating at 37° C. for 30 min. The reaction was stopped with 90 μl of stop buffer (10 mM Tris pH 8.0, 10 mM EDTA) and 1 μl electroporated (Example 8) into electrocompetent E. coli strain, DH10B, (Life Technologies, Gaithersburg, Md.).

The transformed cells were diluted to 1.0 ml with 2×YT broth and 1 μl, 10 μl, 100 μl plated as described in Example 12. Following incubation overnight at 37° C., individual plaques were picked, amplified by PCR with primers A and B, and checked for full-length insert by agarose gel electrophoresis. Clones with full-length insert were sequenced with primers D, E , F, G (Table 3) and checked against the literature. An insert with the correct DNA sequence was amplified by PCR (Example 3) from BS39 with primers A and C (FIG. 5A) and the products run on agarose gel electrophoresis.

Full-length products were excised from the gel and purified as described previously and prepared for cloning by digestion with EcoRI and NcoI. A pBR lac-based expression vector that expressed a murine Fab was prepared to receive this insert by EcoRI and NcoI digestion. This digestion excised the lac promoter and the entire cocking sequence up to the 5'-end of the heavy chain (CH1) constant region (FIG. 5A).

The insert and vector were mixed (2:1 molar ratio) together with 1 μl 10 mM ATP, 1 μl (1 U/μl) T4 DNA ligase, 1 μl 10×ligase buffer in a final volume of 10 μl and ligated overnight at 15° C. The ligation reaction was diluted to 20 μl, and 1 μl electroporated into electrocompetent E. coli strain, DH10B (Example 8), plated on LB tetracycline (10 μg/ml) plates and grown overnight at 37° C.

Clones were picked and grown overnight in 3 ml LB broth supplemented with tetracycline at 20 μg/ml. These clones were tested for the correct insert by PCR amplification (Example 3) with primers A and C, using 1 μl of overnight culture as template. Agarose gel electrophoresis of the PCR reactions demonstrated that all clones had the araCparaB insert. The vector (plasmid) was purified from each culture by Wizard miniprep columns (Promega, Madison, Wis.) following manufacturers recommendations. The new vector contained the araC gene, the araB promoter, the pelB signal sequence, and essentially the entire CH1 region of the heavy chain (FIG. 5B).

The vector was tested for expression by re-introducing the region of the Fab that was removed by EcoRI and NcoI digestion. The region was amplified by PCR, (Example 3) from a plasmid (20 ng) expressing 14F8 with primers H and I (Table 3). The primers, in addition to having sequence specific to 14F8, contain 20 base-pairs of vector sequence at their 5'-end corresponding to the 3'-end of the pelB signal sequence and the 5'-end of the CH1 region for cloning purposes. The PCR products were run on agarose gel electrophoresis and full-length products excised from the gel and purified as described previously.

Figure 6:
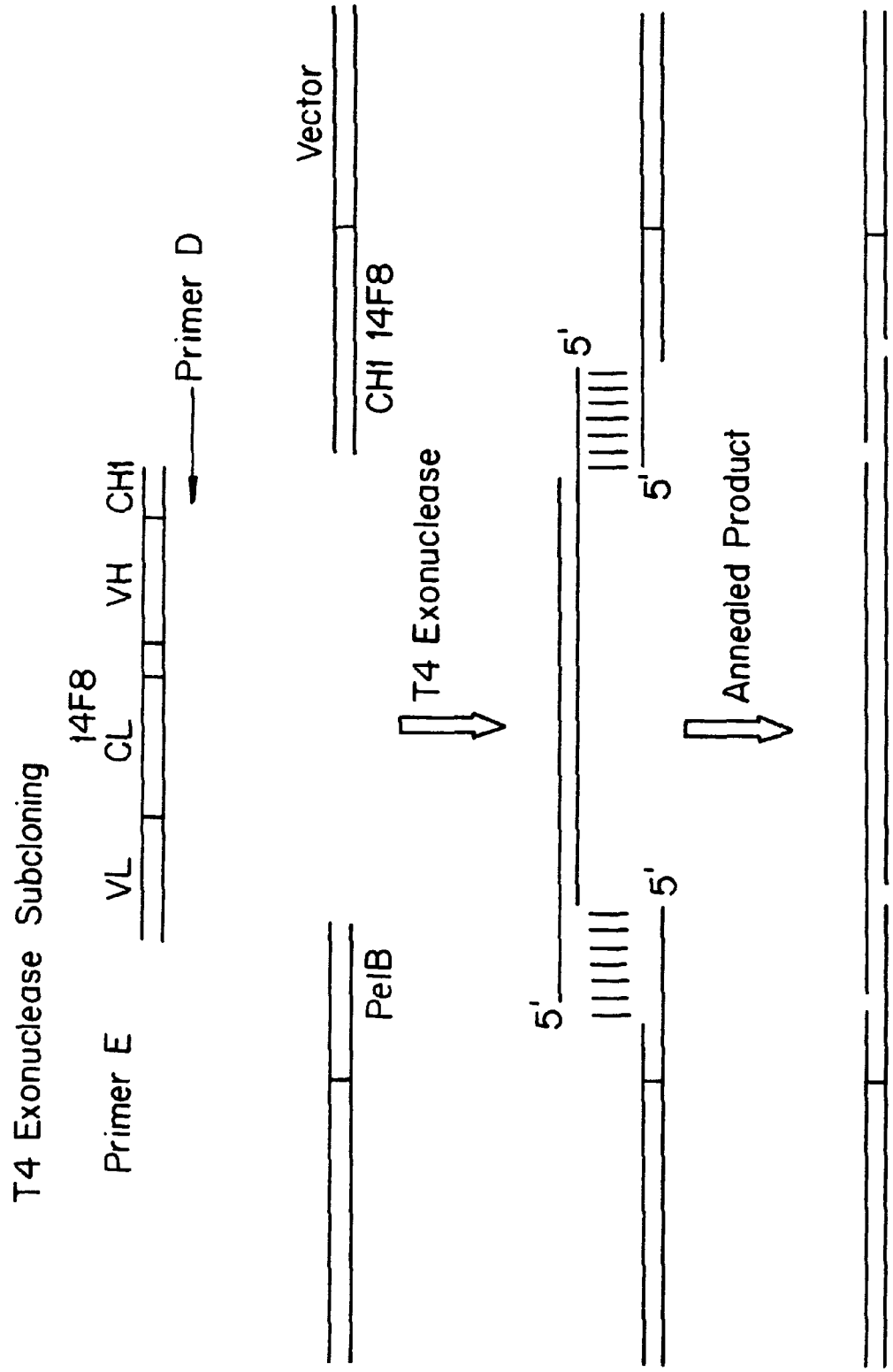
FIG. 6: Subcloning of a DNA segment encoding a Fab by T4 exonuclease digestion.

The vector was linearized with NcoI and together with the insert, prepared for cloning through the 3'→5' exonuclease activity of T4 DNA polymerase. The insert and NcoI digested vector were prepared for T4 exonuclease digestion by aliquoting 1.0 μg of each in separate tubes, adding 1.0 μl of 10×restriction endonuclease Buffer A (Boehringer Mannheim, Indianapolis, Ind.) and bringing the volume to 9.0 μl with water. The samples were digested for 5 min at 30° C. with 1 μl (1 U/μl) of T4 DNA polymerase. The T4 DNA polymerase was heat inactivated by incubation at 70° C. for 15 min. The samples were cooled, briefly spun, and the digested insert (35 ng) and vector (100 ng) mixed together and the volume brought to 10 μl with 1 mM $MgCl_2$. The sample was heated to 70° C. for 2 min and cooled over 20 min to room temperature to allow the complementary 5' single-stranded overhangs of the insert and vector resulting from the exonuclease digestion to anneal together (FIG. 6). The annealed DNA (1.5 μl) was electroporated (Example 8) into 30 μl of electrocompetent E. coli strain DH10B.

The transformed cells were diluted to 1.0 ml with 2×YT broth and 1 μl, 10 μl, and 100 μl plated on LB agar plates supplemented with tetracycline (10 μg/ml) and grown overnight at 37° C. The following day, two clones were picked and grown overnight in 2×YT (10 μg/ml tetracycline) at 37° C. To test protein expression driven from the ara promoter, these cultures were diluted 1/50 in 2×YT(tet) and grown to $OD_{600}$=1.0 at which point they were each split into two cultures, one of which was induced by the addition of arabinose to a final concentration of 0.2% (W/V). The cultures were grown overnight at room temperature, and assayed for Fab production by ELISA. Both of the induced cultures were producing approximately 20 μg/ml Fab. There was no detectable Fab in the uninduced cultures.

Initial efforts to clone polyclonal populations of Fab were hindered by backgrounds of undigested vector ranging from 3–13%. This undigested vector resulted in loss of Fab expressing clones due to the selective advantage non-expressing clones have over Fab expressing clones. A variety of means were tried to eliminate undigested vector from the vector preparations with only partial success; examples including: digesting the vector overnight 37° C. with NcoI, extracting, and redigesting the preparation a second time; including spermidine in the NcoI digest; including single-stranded binding protein (United States Biochemical, Cleveland, Ohio) in the NcoI digest; preparative gel electrophoresis. It was then noted that there is a HindIII restriction site in pBR, 19 base-pairs from the 5'-end of the tetracycline promoter. A vector missing these 19 base-pairs is incapable of supporting growth in the presence of tetracycline, eliminating background due to undigested vector.

The ara-based expression vector was modified to make it tetracycline sensitive in the absence of insert. This was done by digesting the pBRnco vector with NcoI and HindIII (Boehringer Mannheim, Indianapolis, Ind.), which removed the entire antibody gene cassette and a portion of the tet promoter (FIG. 5B). The region excised by NcoI/HindIII digestion was replaced with a stuffer fragment of unrelated DNA by ligation as described above. The ligation reaction was diluted to 20 μl, and 1 μl electroporated (Example 8) into electrocompetent E. coil strain DH10B, plated on LB ampicillin (100 μg/ml) and incubated at 37° C.

After overnight incubation, transformants were picked and grown overnight in LB broth supplemented with ampicillin (100 μg/ml). The vector (plasmid) was purified from each culture by Wizard miniprep columns following manufacturers recommendations. This modified vector, pBRncoH3, is tet sensitive, but still retains ampicillin resistance for growing preparations of the vector.

The antibody gene inserts were amplified by PCR with primers I and J (Table 3) as described in Example 3; primer J containing the 19 base-pairs of the tet promoter removed by HindIII digestion, in addition to 20 base-pairs of vector sequence 3' to the HindIII site for annealing. This modified vector was digested with NcoI/HindIII and, together with the insert, exonuclease digested and annealed as described previously. The tet resistance is restores only in clones that contain an insert capable of completing the tet promoter. The annealed Fab/vector (1 μl) was transformed (Example 8) into 30 μl of electrocompetent E. coli strain, DH10B.

The transformed cells were diluted to 1.0 ml with 2×YT broth and 10 μl of $10^{-2}$ and $10^{-3}$ dilutions plated on LB agar plates supplemented with tetracycline at 10 μg/ml to determine the size of the subcloned polyclonal population. This plating also provides and opportunity to pick individual clones from the polyclonal if necessary. The remaining cells were incubated at 37° C. for 1 hr and then diluted 1/100 into 30 ml 2×YT supplemented with 1% glycerol and 20 μg/ml tetracycline and grown overnight at 37° C. The overnight culture was diluted 1/100 into the same media and grown 8 hr at which time glycerol freezer stocks were made for long term storage at −80° C.

The new vector eliminates growth bias of clones containing vector only, as compared to clones with insert. This, together with the arabinose promoter which is completely repressed in the absence of arabinose, allows cultures of transformed organisms to be expanded without biasing the polyclonal antibody population for antibodies that are better tolerated by E. coli until induction.

A variant of this vector was also constructed to clone any protein with or without a signal sequence. The modified vector has the NcoI restriction site and all of the pelB signal-sequence removed. In its place a NsiI restriction site was incorporated such that upon NsiI digestion and then T4 digestion, there is single base added, in frame, to the araBAD promoter that becomes the adenosine residue (A) of the ATG initiation codon. The HindIII site and restoration of the tetracycline promoter with primer J (Table 3) remains the same as described for the pBRncoH3 vector. Additionally, the T4 exonuclease cloning process is identical to that described above, except that the 5' PCR primer used to amplify the insert contains 20 bp of vector sequence at its 5'-end corresponding to 3'-end of the araBAD promoter rather than the 3'-end of the PelB signal sequence.

Three PCR primers, K, L, and M (Table 3) were used for amplifying the araC regulatory gene (including the araBAD promoter). The 5'-primer, primer K, includes an EcoRI restriction site at its 5'-end for ligating the ara insert into the pBR vector. The 3'-end of the insert was amplified using two primers because a single primer would have been too large to synthesize. The inner 3'-primer (L) introduces the NsiI restriction site, in frame, with the araBAD promoter, with the outer 3' primer (M) introducing the HinDIII restriction site that will be used for ligating the insert into the vector.

The PCR reaction was performed as in Example 3 on a 4×100 μl scale; the reactions containing 100 pmol of 5' primer (K), 1 pmol of the inner 3' primer (L), and 100 pmol of outer 3' primer (M), 10 μl 2 mM dNTPs, 0.5 μL Taq DNA Polymerase, 10 μl 10×Taq DNA polymerase buffer with $MgCl_2$, and $H_2O$ to 100 μL. The araCparaBAD PCR product was precipitated and fractionated by agarose gel electrophoresis and full-length products excised from the gel, purified, resuspended in water, and prepared for cloning by digestion with EcoRI and HinDIII as described earlier. The pBR vector (Life Technologies, Gaithersburg, Md.) was prepared to receive this insert by digestion with EcoRI and HindIII and purification by agarose gel electrophoresis as described above.

The insert and vector were mixed (2:1 molar ratio) together with 1 μl 10 mM ATP, 1 μl (1 U/μl) T4 DNA ligase, 1 μl 10×ligase buffer in a final volume of 10 μl and ligated overnight at 15° C. The ligation reaction was diluted to 20 μl, and 1 μl electroporated into electrocompetent *E. coli* strain, DH10B (Example 8), plated on LB tetracycline (10 μg/ml) plates and grown overnight at 37° C. Clones were picked and grown overnight in 3 ml LB broth supplemented with tetracycline.

These clones were tested for the correct insert by PCR amplification (Example 3) with primers K and M, using 1 μl of overnight culture as template. Agarose gel electrophoresis of the PCR reactions demonstrated that all clones had the araCparaB insert. The vector (plasmid) was purified from each culture by Wizard miniprep columns following manufacturers recommendations. The new vector, pBRnsi contained the araC gene, the araBAD promoter, and a NsiI restriction site.

The vector was tested for expression by introducing a murine Fab. The region was amplified by PCR (Example 3) from a plasmid (20 ng) containing a murine Fab with primers O and N (Table 3). The primers, in addition to having sequence specific to the Fab, contain 20 bp of vector sequence at their 5'-end corresponding to the 3'-end araBAD promoter and the 5'-end of the CH1 region for cloning purposes. The pBRnsi vector was linearized with NsiI and HindIII. The vector and the PCR product were run on an agarose gel, and full-length products were excised from the gel and purified as described previously. The vector and insert were digested with T4 DNA polymerase and annealed as described earlier. The annealed DNA (1 μl) was electroporated (Example 8) into 30 μl of electrocompetent *E. coli* strain DH10B. The transformed cells were diluted to 1.0 ml with 2×YT broth and 1 μl, 10 μl, and 100 μl plated on LB agar plates supplemented with tetracycline (10 μg/ml) and grown overnight at 37° C.

Nitrocellulose lifts were placed on the placed on the surface of the agar plates for 1 min and processed as described (Section 12.24, Molecular Cloning, A laboratory Manual, (1989) Sambrook. J.). The filters were developed with goat anti-kappa-AP, and a positive (kappa expressing) clone was picked and grown overnight in 2×YT (10 μg/ml tetracycline) at 37° C. The vector (plasmid) was purified from the culture by Wizard miniprep columns (Promega, Madison, Wis.) following manufacturers recommendations. The Fab region was excised by NcoI/HindIII digestion and replaced with a stuffer fragment of unrelated DNA by ligation as described above. The ligation reaction was diluted to 20 μl, and 1 μl electroporated (Example 8) into electrocompetent *E. coli* strain DH10B, plated on LB ampicillin (100 μg/ml) and incubated at 37° C. After overnight incubation, transformants were picked and grown overnight in LB broth supplemented with ampicillin (100 μg/ml). The vector (plasmid) was purified from each culture by Wizard miniprep columns following manufacturers recommendations. This modified vector, pBRnsiH3, is tet sensitive, but still retains ampicillin resistance for growing preparations of the vector.

Example 18

Subcloning Monoclonal and Polyclonal Fab Populations into Expression Vectors and Electroporation into *Escherichia coli*

The final round of the polyclonal glutamate dehydrogenase antibody phage (see Example 16) was diluted 1/30 in 2×YT (approximately 2×10⁹/ml) and 1 μl used as template for PCR amplification of the antibody gene inserts with primers I and P (Table 3). PCR (3–100 μL reactions) was performed using a high-fidelity PCR system, Expand (Boehringer Mannheim, Indianapolis, Ind.) to minimize errors incorporated into the DNA product. Each 100 μl reaction contained 100 pmol of 5' primer I, 100 pmol of 3' primer J, 0.7 units of Expand DNA polymerase, 10 μl 2 mM dNTPs, 10 μl 10×Expand reaction buffer, 1 μl diluted phage stock as template, and water to 100 μl. The reaction was carried out in a Perkin-Elmer thermal cycler (Model 9600) using the following thermal profile: one cycle of denaturation at 94° C. (1 min); ten cycles of denaturation (15 sec, 94° C.), annealing (30 sec, 55° C.), elongation (60 sec, 72° C.); fifteen cycles of denaturation (15 sec, 94° C.), annealing (30 sec, 55° C.), elongation (80 sec plus 20 sec for each additional cycle, 72° C.); elongation (6 min, 72° C.); soak (4° C., indefinitely). The PCR products were ethanol precipitated, pelleted and dried as described above. The DNA was dissolved in water and fractionated by agarose gel electrophoresis. Only full-length products were excised from the gel, purified, and resuspended in water as described earlier.

The insert and NcoI/HindIII digested pBRncoH3 vector were prepared for T4 exonuclease digestion by adding 1.0 μl of 10×Buffer A to 1.0 μg of DNA and bringing the final volume to 9 μl with water. The samples were digested for 4 min at 30° C. with 1 μl (1 U/μl) of T4 DNA polymerase. The T4 DNA polymerase was heat inactivated by incubation at 70° C. for 10 min. The samples were cooled, briefly spun, and 5 μl of the digested antibody gene insert and 2.0 μl of 10×annealing buffer were mixed with 5 μL of digested vector in a 1.5 mL tube. The volume was brought to 20 μl with water, heated to 70° C. for 2 min and cooled over 20 min to room temperature to allow the insert and vector to anneal.

The insert and vector were ligated together by adding 2 μl of 10×synthesis buffer, 2 μl T4 DNA ligase (1 U/μl), 2 μl diluted T7 DNA polymerase (1 U/μl) and incubating at 37° C. for 30 min. The reaction was stopped with 370 μl of stop buffer (10 mM Tris pH 8.0, 10 mM EDTA), extracted with phenol/chloroform, chloroform, and precipitated from ethanol at −20° C. The reaction was centrifuged and the supernatant aspirated. The sample was briefly spun an additional time and all traces of ethanol removed with a pipetman. The pellet was dried in vacuo.

The DNA was resuspended in 2 μl of water and 1 μl electroporated (Example 8) into 40 μl of electrocompetent *E. coli* strain, DH10B. The transformed cells were diluted to 1.0 ml with 2×YT broth and 10 μl of $10^{-1}$, $10^{-2}$ and $10^{-3}$ dilutions plated on LB agar plates supplemented with tetracycline at 10 μg/ml to determine the size of the subcloned polyclonal population. The remaining cells were incubated at 37° C. for 1 hr and then diluted 1/100 into 30 ml 2×YT supplemented with 1% glycerol and 20 μg/ml tetracycline and grown overnight at 37° C. The overnight culture was diluted 1/100 into the same media, grown 8 hr, and glycerol freezer stocks made for long term storage at −80° C. The polyclonal antibody was designated CD.43.5.PC.

The monoclonal antibody to glutamate dehydrogenase (Example 16) was also subcloned following the same general procedure described above. The subcloned monoclonal antibody was designated CD.43.9. The polyclonal antibody phage stock for *Clostridium difficile* toxin A (Example 15) was subcloned in a similar way. The subcloned polyclonal antibody was designated CD.TXA.1.PC.

Example 19
Cloning of *Clostridium difficile* Glutamate Dehydrogenase (the Target for Panning in Example 15)

PCR primers were made corresponding to the coding sequence at the 5'-end of glutamate dehydrogenase, and the coding sequence at the 3'-end of glutamate dehydrogenase, including six histidine codons inserted between the end of the coding sequence and the stop codon to assist in purification of the recombinant protein by metal-chelate chromatography, primers Q and R, respectively (Table 3). In addition, the 5' primer contains 20 base-pairs of vector sequence at its 5'-end corresponding to the 3'-end of the pBRnsiH3 vector. The 3' primer contains the 19 base-pairs of tet promoter removed by HindIII digestion, in addition to 20 base-pairs of vector sequence 3' to the HindIII site at its 5' end (Example 17).

The PCR amplification of the glutamate dehydrogenase gene insert was done on a 100 μl reaction scale containing 100 pmol of 5' primer (Q), 100 pmol of 3' primer (R), 2 units of Expand polymerase, 10 μl 2 mM dNTPs, 10 μl 10×Expand reaction buffer, 1 μl *C. difficile* genomic DNA (75 ng) as template, and water to 100 μl. The reaction was carried out in a Perkin-Elmer thermal cycler as described in Example 18. The PCR products were precipitated and fractionated by agarose gel electrophoresis and full-length products excised from the gel, purified, and resuspended in water (Example 17). The insert and NsiI/HindIII digested pBRnsiH3 vector were prepared for T4 exonuclease digestion by adding 1.0 μl of 10×Buffer A to 1.0 μg of DNA and bringing the final volume to 9 μl with water. The samples were digested for 4 min at 30° C. with 1 μl (1 U/μl) of T4 DNA polymerase. The T4 DNA polymerase was heat inactivated by incubation at 70° C. for 10 min. The samples were cooled, briefly spun, and 70 ng of the digested insert added to 100 ng of digested pBRnsiH3 vector in a fresh microfuge tube. After the addition of 1 μl of 10×annealing buffer, the volume was brought to 10 μl with water and the mixture heated to 70° C. for 2 min and cooled over 20 min to room temperature. The annealed DNA was diluted one to four with distilled water and electroporated (Example 8) into 30 μl of electrocompetent *E. coli* strain, DH10B. The transformed cells were diluted to 1.0 ml with 2×YT broth and 10 μl, 100 μl and 300 μl plated on LB agar plates supplemented with tetracycline (10 μg/ml) and grown overnight at 37° C. Clones were picked and grown overnight in 2×YT (10 μg/ml tetracycline) at 37° C. The following day glycerol freezer stocks made for long term storage at −80° C. The glutamate dehydrogenase clone was grown and purified on a preparative scale as described in Example 20.

Example 20

Growth of *E. coli* Cultures and Purification of Recombinant Antibodies and Antigens A shake flask inoculum is generated overnight from a −70° C. cell bank in an Innova 4330 incubator shaker (New Brunswick Scientific, Edison, N.J.) set at 37° C., 300 rpm. The inoculum is used to seed a 20 L fermenter (Applikon, Foster City, Calif.) containing defined culture medium (Pack et al., *Bio/Technology* 11, 1271–1277 (1993)) supplemented with 3 g/L L-leucine, 3 g/L L-isoleucine, 12 g/L casein digest (Difco, Detroit, Mich.), 12.5 g/L glycerol and 10 mg/ml tetracycline. The temperature, pH and dissolved oxygen in the fermenter are controlled at 26° C., 6.0–6.8 and 25% saturation, respectively. Foam is controlled by addition of polypropylene glycol (Dow, Midland, Mich.). Glycerol is added to the fermenter in a fed-batch mode. Fab expression is induced by addition of L(+)-arabinose (Sigma, St. Louis, Mo.) to 2 g/L during the late logarithmic growth phase. Cell density is measured by optical density at 600 nm in an UV-1201 spectrophotometer (Shimadzu, Columbia, Md.). Final Fab concentrations are typically 100–500 mg/L. Following run termination and adjustment of pH to 6.0, the culture is passed twice through an M-210B-EH Microfluidizer (Microfluidics, Newton, Mass.) at 17000 psi. The high pressure homogenization of the cells releases the Fab into the culture supernatant.

The first step in purification is expanded bed immobilized metal affinity chromatography (EB-IMAC). Streamline Chelating resin (Pharmacia, Piscataway, N.J.) is charged with 0.1 M $NiCl_2$. It is then expanded and equilibrated in 50 mM acetate, 200 mM NaCl, 10 mM imidazole, 0.01% $NaN_3$, pH 6.0 buffer flowing in the upward direction. A stock solution is used to bring the culture homogenate to 10 mM imidazole, following which, it is diluted two-fold or higher in equilibration buffer to reduce the wet solids content to less than 5% by weight. It is then loaded onto the Streamline column flowing in the upward direction at a superficial velocity of 300 cm/hr. The cell debris passes through unhindered, but the Fab is captured by means of the high affinity interaction between nickel and the hexahistidine tag on the Fab heavy chain. After washing, the expanded bed is converted to a packed bed and the Fab is eluted with 20 mM borate, 150 mM NaCl, 200 mM imidazole, 0.03% $NaN_3$, pH 8.0 buffer flowing in the downward direction. The second step in purification uses ion-exchange chromatography (IEC). Q Sepharose FastFlow resin (Pharmacia, Piscataway, N.J.) is equilibrated in 20 mM borate, 37.5 mM NaCl, 0.01% $NaN_3$, pH 8.0. The Fab elution pool from the EB-IMAC step is diluted four-fold in 20 mM borate, 0.01% $NaN_3$, pH 13.0 and loaded onto the IEC column. After washing, the Fab is eluted with a 37.5–200 mM NaCl salt gradient. The elution fractions are evaluated for purity using an Xcell II SDS-PAGE system (Novex, San Diego, Calif.) prior to pooling. Finally, the Fab pool is concentrated and diafiltered into 20 mM borate, 150 mM NaCl, 0.01% $NaN_3$, pH 8.0 buffer for storage. This is achieved in a Sartocon Slice system fitted with a 10,000 MWCO cassette (Sartorius, Bohemia, N.Y.). The final purification yields are typically 50%. The concentration of the purified Fab is measured by UV absorbance at 280 nm, assuming an absorbance of 1.6 for a 1 mg/mL solution.

Expression of Antigen or Antibodies in Shake Flasks and Purification

A shake flask inoculum is generated overnight from a −70° C. cell bank in an incubator shaker set at 37° C., 300 rpm. The cells are cultured in a defined medium described above. The inoculum is used to seed a 2 L Tunair shake flask (Shelton Scientific, Shelton, Conn.) which is grown at 37° C., 300 rpm. Expression is induced by addition of L(+)-arabinose to 2 g/L during the logarithmic growth phase, following which, the flask is maintained at 23° C., 300 rpm. Following batch termination, the culture is passed through an M-110Y Microfluidizer (Microfluidics, Newton, Mass.) at 17000 psi. The homogenate is clarified in a J2-21 centrifuge (Beckman, Fullerton, Calif.).

Purification employs immobilized metal affinity chromatography. Chelating Sepharose FastFlow resin (Pharmacia, Piscataway, N.J.) is charged with 0.1 M $NiCl_2$ and equilibrated in 20 mM borate, 150 mM NaCl, 10 mM imidazole, 0.01% $NaN_3$, pH 8.0 buffer. A stock solution is used to bring the culture supernatant to 10 mM imidazole. The culture supernatant is then mixed with the resin and incubated in the incubator shaker set at room temperature, 150–200 rpm. The antigen is captured by means of the high affinity interaction between nickel and the hexahistidine tag on the antigen. The culture supernatant and resin mixture is poured into a chromatography column. After washing, the antigen is eluted with 20 mM borate, 150 mM NaCl, 200 mM imidazole, 0.01% $NaN_3$, pH 8.0 buffer. The antigen pool is concentrated in a stirred cell fitted with a 10,000 MWCO membrane (Amicon, Beverly, Mass.). It is then dialysed overnight into 20 mM borate, 150 mM NaCl, 0.01% $NaN_3$, pH 8.0 for storage, using 12–14,000 MWCO dialysis tubing. The purified antigen is evaluated for purity by SDS-PAGE analysis. A yield of 150 mg of purified antigen per liter of shake flask culture is expected. The concentration of the *C. difficile* glutamate dehydrogenase antigen is based on UV absorbance at 280 nm, assuming an absorbance of 1.48 for a 1 mg/mL solution. Antibody shake flask expression and purification is done as described for antigen.

Example 21

Preparation of 7F11 Monoclonal Antibody Synthesis of Acetylthiopropionic Acid

To a stirred solution of 3-mercaptopropionic acid (7 ml, 0.08 moles) and imidazole (5.4 g, 0.08 moles) in tetrahydrofuran (THF, 700 ml) was added dropwise over 15 min, under argon, a solution of 1-acetylimidazole (9.6 g, 0.087 moles) in THF (100 ml). The solution was allowed to stir a further 3 hr at room temperature after which time the THF was removed in vacuo. The residue was treated with ice-cold water (18 ml) and the resulting solution acidified with ice-cold concentrated HCl (14.5 ml) to pH 1.5–2. The mixture was extracted with water (2×50 ml), dried over magnesium sulfate and evaporated. The residual crude yellow oily solid product (10.5 g) was recrystallized from chloroform-hexane to afford 4.8 g (41% yield) acetylthiopropionic acid as a white solid with a melting point of 44–45° C.

Decapeptide (SEQ ID NO:1) Derivatives

The decapeptide, YPYDVPDYAS, (Chiron Mimotopes Peptide Systems, San Diego, Calif.) was dissolved (0.3 g) in dry DMF (5.4 mL) in a round bottom flask under argon with moderate stirring. Imidazole (0.02 g) was added to the stirring solution. Separately, acetylthiopropionic acid (0.041 g) was dissolved in 0.55 mL of dry DMF in a round bottom flask with stirring and 0.056 g of 1,1'-carbonyldiimidazole (Aldrich Chemical Co., Milwaukee, Wis.) was added to the stirring solution. The flask was sealed under argon and stirred for at least 30 min at room temperature. This solution was added to the decapeptide solution and the reaction mixture was stirred for at least six hr at room temperature before the solvent was removed in vacuo. The residue in the flask was triturated twice using 10 mL of diethyl ether each time and the ether was decanted. Methylene chloride (20 mL) was added to the residue in the flask and the solid was scraped from the flask and filtered using a fine fritted Buchner funnel. The solid was washed with an additional 20 mL of methylene chloride and the Buchner funnel was dried under vacuum. In order to hydrolyze the derivative to generate a free thiol, it was dissolved in 70% DMF and 1 N potassium hydroxide was added to a final concentration of 0.2 N while mixing vigorously. The derivative solution was allowed to stand for 5 min at room temperature prior to neutralization of the solution by the addition of a solution containing 0.5 M potassium phosphate, 0.1 M borate, pH 7.0, to which concentrated hydrochloric acid has been added to a final concentration of 1 M. The thiol concentration of the hydrolyzed decapeptide derivative was determined by diluting 10 μL of the solution into 990 μL of a solution containing 0.25 mM 5,5'-dithiobis(2-nitrobenzoic acid) (DTNB, Aldrich Chemical Co., Milwaukee Wis.) and 0.2 M potassium borate, pH 8.0. The thiol concentration in mM units was equal to the $A_{412}(100/13.76)$.

Preparation of Conjugates of Decapeptide Derivative with Keyhole Limpet Hemocyanin and Bovine Serum Albumin Keyhole limpet hemocyanin (KLH, 6 ml of 14 mg/ml, Calbiochem, San Diego, Calif.) was reacted with sulfosuccinimidyl 4-(N-maleimidomethyl)cyclohexane-1-carboxylate (SULFO-SMCC) by adding 15 mg of SULFO-SMCC and maintaining the pH between 7 and 7.5 with 1N potassium hydroxide over a period of one hr at room temperature while stirring. The protein was separated from the unreacted SULFO-SMCC by gel filtration chromatography in 0.1 M potassium phosphate, 0.02 M potassium borate, and 0.15 M sodium chloride, pH 7.0, and 24 ml of KLH-maleimide was collected at a concentration of 3.1 mg/ml. The hydrolyzed decapeptide derivative was separately added to portions of the KLH-maleimide in substantial molar excess over the estimated maleimide amounts present and the solution was stirred for 4 hr at 4° C. and then each was dialyzed against 3 volumes of one liter of pyrogen-free phosphate-buffered saline, pH7.4, prior to immunization.

Bovine serum albumin (BSA, 3.5 ml of 20 mg/ml) was reacted with SMCC by adding a solution of 6.7 mg of SMCC in 0.3 ml acetonitrile and stirring the solution for one hr at room temperature while maintaining the pH between 7 and 7.5 with 1N potassium hydroxide. The protein was separated from unreacted materials by gel filtration chromatography in 0.1 M potassium phosphate, 0.02 M potassium borate, 0.15 M sodium chloride, pH 7.0. The hydrolyzed decapeptide derivative was separately added to portions of the BSA-maleimide in substantial molar excess over the estimated maleimide amounts present and the solution was stirred for 4 hr at 4° C. The solutions were used to coat microtiter plates for the detection of antibodies that bound to the decapeptide derivative by standard techniques.

Production and Primary Selection of Monoclonal Antibodies

Immunization of Balb/c mice was performed according to the method of Liu et al. *Clin Chem* 25, 527–538 (1987).

Fusions of spleen cells with SP2/0-Ag 14 myeloma cells, propagation of hybridomas, and cloning were performed by standard techniques. Selection of hybridomas for further cloning began with culture supernatant at the 96-well stage. A standard ELISA procedure was performed with a BSA conjugate of decapeptide derivative adsorbed to the ELISA plate. Typically, a single fusion was plated out in twenty plates and approximately 10–20 wells per plate were positive by the ELISA assay. At this stage, a secondary selection could be performed if antibodies to the SMCC part of the linking arm were to be eliminated from further consideration. An ELISA assay using BSA derivatized with SMCC but not linked to the decapeptide derivative identified which of the positive clones that bound the BSA conjugates were actually binding the SMCC-BSA. The antibodies specific for SMCC-BSA may be eliminated at this step. Monoclonal antibody 7F11, specific for the decapeptide derivative, was produced and selected by this process.

Example 22
Preparation of 7F11 Magnetic Latex
MAG/CM-BSA

To 6 mL of 5% magnetic latex (MAG/CM, 740 μm 5.0%, Seradyn, Indianapolis, Ind.) was added 21 mL of water followed by 3 mL of 600 mM 2-(4-morpholino)-ethane sulfonic acid, pH 5.9 (MES, Fisher Scientific, Pittsburgh, Pa.). Homocysteine thiolactone hydrochloride (HCTL, 480 mg, Aldrich Chemical Co., Milwaukee, Wis.) and 1-(3-Dimethylaminopropyl)-3-ethylcarbodiimide (EDAC, 660 mg, Aldrich Chemical Co., Milwaukee, Wis.) were added in succession, and the reaction mixture was rocked at room temperature for 2 h. The derivatized magnetic latex was washed 3 times with 30 mL of water (with magnet as in Example 14) using probe sonication to resuspend the particles. The washed particles were resuspended in 30 mL of water. Three mL of a solution containing sodium hydroxide (2M) and EDTA (1 mM) was added to the magnetic latex-HCTL suspension, and the reaction proceeded at room temperature for 5 min. The pH was adjusted to 6.9 with 6.45 mL of 1 M hydrochloric acid in 500 mM sodium phosphate, 100 mM sodium borate. The hydrolyzed magnetic latex-HCTL was separated from the supernate with the aid of a magnet, and then resuspended in 33 mL of 50 mM sodium phosphate, 10 mM sodium borate, 0.1 mM EDTA, pH 7.0. The magnetic latex suspension was then added to 2 mL of 36 mg mL$^{-1}$ BSA-SMCC (made as described in Example 21 with a 5-fold molar excess of SMCC over BSA), and the reaction mixture was rocked overnight at room temperature. N-Hydroxyethylmaleimide (NHEM, 0.42 mL of 500 mM, Organix Inc., Woburn, Mass.) was added to cap any remaining thiols for 30 min. After 30 min, the magnetic latex-BSA was washed twice with 30 mL of 50 mM potassium phosphate, 10 mM potassium borate, 150 mM sodium chloride, pH 7.0 (50/10/150) and twice with 30 mL of 10 mM potassium phosphate, 2 mM potassium borate, 200 mM sodium thiocyanate, pH 7.0 (10/2/200). The magnetic latex-BSA was resuspended in 30 mL of 10/2/200.

7F11-SH (1:5)

To a solution of 7F11 (3.8 mL of 5.85 mg mL-1) was added 18 μL of SPDP (40 mM in acetonitrile). The reaction proceeded at room temperature for 90 min after which taurine (Aldrich Chemical Co., Milwaukee, Wis.) was added to a final concentration of 20 mM. Fifteen min later DTT was added to a final concentration of 2 mM, and the reduction reaction proceeded at room temperature for 30 min. The 7F11-SH was purified on G-50 (40 mL) that was eluted with 50/10/150 plus 0.1 mM EDTA. The pool of purified 7F11-SH was reserved for coupling to the MAG/CM-BSA-SMCC.

MAG/CM-BSA-7F11

SMCC (10 mg) was dissolved in 0.5 mL of dry dimethylformamide (Aldrich Chemical Co., Milwaukee, Wis.), and this solution was added to the magnetic latex-BSA suspension. The reaction proceeded at room temperature with gentle rocking for 2 h. Taurine was added to a final concentration of 20 mM. After 20 min the magnetic latex-BSA-SMCC was separated from the supernate with the aid of a magnet and then resuspended in 10/2/200 (20 mL) with probe sonication. The magnetic latex was purified on a column of Superflow-6 (240 mL, Sterogene Bioseparations Inc., Carlsbad, Calif.) that was eluted with 10/2/200. The buffer was removed, and to the magnetic latex cake was added 30 mL of 0.7 mg mL$^{-1}$ 7F11-SH. The reaction mixture was rocked overnight at room temperature. After 20 hr the reaction was quenched with mercaptoethanol (2 mM, Aldrich Chemical Co., Milwaukee, Wis.) followed by NHEM (6 mM). The MAG/CM-7F11 was washed with 10/2/200 followed by 50/10/150. The magnetic latex was then resuspended in 30 mL of 50/10/150.

TABLE 3

PCR and Sequencing Primer
Sequence (SEQ ID NOS:2–19)

A  5' (CACTCAACCCTATCTATTAATGTGAATTCAAATGGACGAAGC
       AGGGATTC)

B- 5' (GTAGGCAATAGGTATTTCATCGTTTCACTCCATCCAAA)

C- 5' (TCCGTGCCGGTTGTGAAG)

D- 5' (TACGCGAGGCTTGTCAGT)

E- 5' (TTCATCACTACGGTCGTC)

F- 5' (GACGGCAATGTCTGATGC)

G- 5' (GATATCAACGTTTATCTAATCAGGCCATGGCTGGTTGGGCAG

H- 5' (GGCATCCCAGGGTCACCATG)

I- 5' (TCGCTGCCCAACCAGCCATG)

J- 5' (GTGATAAACTACCGCATTAAAGCTTATCGATGATAAGCTGTCA
       ATTAAGAATCCCTGGGCACAATTTTC)

K- 5' (AGAGCTGCAGAATTCAGCTGATCATCTCACCAATAAAAAACGC
       CCGGCGGCAACCGAGCGTTCTGAACAAATGGACGAAG
       CAGGGATTC)

L- 5' (TCTCTCCAAGGAAGCTTAAAAAAAAGCCCGCTCATTAGGCGGG
       CTAGCTTAATCAATCATGCATCGTTTCACTCCATCCA
       AAAAAAC)

M- 5' (ACAGGTACGAAGCTTATCGATGATAAGCTGTCAAACCAAGGAC
       CTTAAAAAAAAGCCCGCTCATTAGGC)

N- 5' (ACCCGTTTTTTTGGATGGAGTGAAACGATGCATTACCTATTGC
       CTACGGCA)

O- 5' (GTGATAAACTACCGCATTAAAGCTTATCGATGATAAGCTGTCA
       ATTAAGAAGCGTAGTAGTCCGGAACGTC)

P- 5' (GTGATAAACTACCGCATTAAAGCTTATCGATGATAAGCTGTCA
       ATTAGTGATGGTGATGGTGATGACAATCCCTG)

Q  5' (ACCCGTTTTTTTGGATGGAGTGAAACGATGTCAGG
       AAAAGATGTAAATGTC)

R- 5' (GTGATAAACTACCGCATTAAAGCTTATCGA
       TGATAAGCTGTCAATTAGTGATGGT
       GATGGTGATGGTACCATCCTCTTAATTTCATAGC)

Note: restriction enzyme sites are in bold type.
GAATTC = EcoRI

TABLE 3-continued

PCR and Sequencing Primer
Sequence (SEQ ID NOS:2—19)

CCATGG = NcoI
AAGCTT = HindIII

---

What is claimed is:

1. A method of producing a multivalent polypeptide display library, comprising:
   (a) providing a library of replicable genetic packages, wherein a member comprises a replicable genetic package capable of displaying from its outersurface a fusion protein comprising polypeptide to be screened and a tag, which fusion protein is encoded by a segment of a genome of the package, the polypeptide varying between library members, the number of copies of the fusion protein displayed per library member varying between library members, and the tag being the same in different library members; and
   (b) contacting the library with a receptor having a specific affinity for the tag under conditions whereby library members displaying at least two copies of the fusion protein are preferentially bound to immobilized receptor by multivalent bonds between the receptor and the at least two copies of the tag;
   (c) separating library members bound to the immobilized receptor from unbound library members to produce a sublibrary enriched relative to the library for members displaying at least two copies of the fusion protein.

2. The method of claim 1, wherein the replicable genetic package is a phage.

3. The method of claim 2, wherein the polypeptide to be screened is an antibody chain.

4. The method of claim 3, wherein the polypeptide to be screened is a single-chain antibody comprising a heavy chain variable domain, peptide spacer and a light chain variable domain.

5. The method of claim 3, wherein the polypeptide to be screened comprises an antibody heavy or light chain variable domain, and in at least some library members, the heavy or light chain variable domain is respectively complexed with a partner light or heavy chain antibody variable domain to form a Fab fragment.

6. The method of claim 5, wherein the partner light or heavy chain antibody variable domain is linked to a second tag.

7. The method of claim 6, wherein the fusion protein is encoded by a first segment of the genome, and the partner light or heavy chain antibody variable domain and the second tag are encoded by a second segment of the same genome.

8. The method of claim 7, further comprising contacting the library or fraction thereof with a second receptor having a specific affinity for the second tag under conditions whereby library members displaying at least two copies of the second fusion protein are preferentially bound to immobilized second receptor by multivalent bonds between the immobilized receptor and the at least two copies of the second tag;

separating library members bound to the immobilized second receptor from unbound library members to produce a second sublibrary enriched relative to the library for members displaying at least two copies of the second fusion protein.

9. The method of claim 1, further comprising (d) contacting the sublibrary with a target lacking specific affinity for the tag, and separating library members bound to the target via their displayed polypeptides from unbound library members.

10. The method of claim 1, wherein the receptor is immobilized to support during the contacting step.

11. A method of producing a multivalent Fab phage display library, comprising:

providing a library of phage, wherein a library member comprises a phage capable of displaying from its outersurface a fusion protein comprising a phage coat protein, an antibody light or heavy chain variable domain, and a tag, wherein in at least some members, the antibody heavy or light chain is complexed with a partner antibody heavy or light chain variable domain chain, the complex forming a Fab fragment to be screened, wherein the fusion protein and/or the partner antibody heavy or light chain are encoded by segment(s) of the genome of the phage, and the number of copies of the fusion protein and the partner antibody chain displayed per phage vary between library members;

contacting the library or a fraction thereof with a receptor having a specific affinity for the tag under conditions whereby library members displaying at least two copies of the fusion protein are preferentially bound to immobilized receptor by multivalent bonds between the receptor and the at least two copies of the tag;

separating library members bound to the receptor from unbound library members to produce an sublibrary enriched relative to the library for members displaying at least two copies of the fusion protein.

12. A method of producing a multivalent Fab phage display library, comprising:

providing a library of phage, wherein a library member comprises a phage capable of displaying from its outersurface a fusion protein comprising a phage coat protein, and an antibody light or heavy chain variable domain, wherein in at least some members, the antibody heavy or light chain is complexed with a partner antibody heavy or light chain variable domain chain fused to a tag, the complex forming a Fab fragment to be screened, wherein the fusion protein and/or the partner antibody heavy or light chain fused to the tag are encoded by segment(s) of the genome of the phage, and the number of copies of the fusion protein and the partner antibody chain displayed per phage vary between library members;

contacting the library or a fraction thereof with a receptor having a specific affinity for the tag under conditions whereby library members displaying at least two copies of the partner antibody chain are preferentially bound to immobilized receptor by multivalent bonds between the immobilized receptor and the at least two copies of the tag;

separating library members bound to the receptor from unbound library members to produce an sublibrary enriched relative to the library for members displaying at least two copies of the partner antibody chain.

13. The method of claim 11 or 12, further comprising:

contacting the sublibrary with a target lacking specific affinity for the tag and separating library members bound to the target via their displayed Fab fragments from unbound library members.

14. The method of claim 13, further comprising subcloning DNA segment(s) encoding the antibody heavy or light chain and/or the partner antibody light or heavy chain from a bound library member to an expression vector;

introducing the expression vector into a host and expressing the DNA segment(s) in the host to produce a Fab fragment having affinity for the target.

15. The method of claim 14, wherein the DNA segment(s) is/are subcloned from a plurality of library members and expressed in the host to produce a plurality of Fab fragments having affinity for the target.

16. The method of claim 15, further comprising formulating the plurality of Fab fragments with a diagnostic or therapeutic excipient.

17. A method of producing a multivalent Fab phage display library, comprising:

providing a library of phage, wherein a library member comprises a phage displaying from its outersurface a fusion protein comprising an antibody light or heavy chain variable domain and a tag, wherein in at least some members, the antibody heavy or light chain is complexed with a second fusion protein comprising a partner antibody heavy or light chain variable domain and a second tag, the complex forming a Fab fragment to be screened, wherein the fusion protein and/or the second fusion protein are encoded by segment(s) of the genome of the phage, the number of copies of the fusion protein displayed per phage varies between library members and the number of copies of the second fusion protein displayed per phage varies between library members;

contacting the library or a fraction thereof with a receptor having a specific affinity for the tag under conditions whereby library members displaying at least two copies of the fusion protein are preferentially bound to immobilized receptor by formation of multivalent bonds between the receptor and the at least two copies of the tag;

separating library members bound to the receptor from unbound library members to produce an sublibrary enriched relative to the library for members displaying at least two copies of the fusion protein;

contacting the library or a second fraction thereof with a second receptor having a specific affinity for the second tag under conditions whereby library members displaying at least two copies of the second fusion protein are preferentially bound to the second receptor by multivalent bonds between the second receptor and the least two copies of the second tag;

separating library members bound to the second receptor from unbound library members to produce a second sublibrary enriched relative to the library for members displaying at least two copies of the second fusion protein.

18. The method of claim 17, whereby the second fraction is the sublibrary and the second sublibrary is enriched relative to the library for members displaying at least two copies of the fusion protein and at least two copies of the second fusion protein forming two copies of a Fab fragment.

19. The method of claim 9, further comprising performing a further cycle of steps (a)–(d), wherein library members bound to the target in step (d) of the first cycle form the library of genetic packages in step (a) of the further cycle.

* * * * *

SEQUENCE LISTING (1) GENERAL INFORMATION:

(iii) NUMBER OF SEQUENCES: 85

(2) INFORMATION FOR SEQ ID NO:1:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:1:

Tyr Pro Tyr Asp Val Pro Asp Tyr Ala Ser
 1               5                   10

(2) INFORMATION FOR SEQ ID NO:2:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

CACTCAACCC TATCTATTAA TGTGGAATTC AAATGGACGA AGCAGGGATT C           51

(2) INFORMATION FOR SEQ ID NO:3:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

GTAGGCAATA GGTATTTCAT CGTTTCACTC CATCCAAA                          38

(2) INFORMATION FOR SEQ ID NO:4:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

TCCGTGCCGG TTGTGAAG                                                18

(2) INFORMATION FOR SEQ ID NO:5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

TACGCGAGGC TTGTCAGT                                          18

(2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

TTCATCACTA CGGTCGTC                                          18

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

GACGGCAATG TCTGATGC                                          18

(2) INFORMATION FOR SEQ ID NO:8:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

GATATCAACG TTTATCTAAT CAGGCCATGG CTGGTTGGGC AG                42

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

GGCATCCCAG GGTCACCATG                                         20

(2) INFORMATION FOR SEQ ID NO:10:

(i) SEQUENCE CHARACTERISTICS:

(A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

TCGCTGCCCA ACCAGCCATG                                               20

(2) INFORMATION FOR SEQ ID NO:11:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

GTGATAAACT ACCGCATTAA AGCTTATCGA TGATAAGCTG TCAATTAAGA ATCCCTGGGC    60

ACAATTTTC                                                           69

(2) INFORMATION FOR SEQ ID NO:12:

(i) SEQUENCE CHARACTERISTICS:
        (A) LENGTH: 89 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

AGAGCTGCAG AATTCAGCTG ATCATCTCAC CAATAAAAAA CGCCCGGCGG CAACCGAGCG    60

TTCTGAACAA ATGGACGAAG CAGGGATTC                                     89

(2) INFORMATION FOR SEQ ID NO:13:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

TCTCTCCAAG GAAGCTTAAA AAAAAGCCCG CTCATTAGGC GGGCTAGCTT AATCAATCAT    60

GCATCGTTTC ACTCCATCCA AAAAAAC                                       87

(2) INFORMATION FOR SEQ ID NO:14:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

ACAGGTACGA AGCTTATCGA TGATAAGCTG TCAAACCAAG GAGCTTAAAA AAAAGCCCGC    60

TCATTAGGC                                                           69

(2) INFORMATION FOR SEQ ID NO:15:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

```
ACCCGTTTTT TTGGATGGAG TGAAACGATG CATTACCTAT TGCCTACGGC A            51
```

(2) INFORMATION FOR SEQ ID NO:16:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

```
GTGATAAACT ACCGCATTAA AGCTTATCGA TGATAAGCTG TCAATTAAGA AGCGTAGTAG   60

TCCGGAACGT C                                                      71
```

(2) INFORMATION FOR SEQ ID NO:17:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

```
GTGATAAACT ACCGCATTAA AGCTTATCGA TGATAAGCTG TCAATTAGTG ATGGTGATGG   60

TGATGACAAT CCCTG                                                  75
```

(2) INFORMATION FOR SEQ ID NO:18:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

```
ACCCGTTTTT TTGGATGGAG TGAAACGATG TCAGGAAAAG ATGTAAATGT C            51
```

(2) INFORMATION FOR SEQ ID NO:19:

(i) SEQUENCE CHARACTERISTICS:
        (A) LENGTH: 89 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

```
GTGATAAACT ACCGCATTAA AGCTTATCGA TGATAAGCTG TCAATTAGTG ATGGTGATGG   60
```

```
TGATGGTACC ATCCTCTTAA TTTCATAGC                                              89

(2) INFORMATION FOR SEQ ID NO:20:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

TTACCCCTGT GGCAAAAGCC GAGGTGCAGC TTCAGGAGTC AGG                               43

(2) INFORMATION FOR SEQ ID NO:21:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

TTACCCCTGT GGCAAAAGCC CAGGTCCAGC TGCAGCAGTC TGG                               43

(2) INFORMATION FOR SEQ ID NO:22:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:22:

TTACCCCTGT GGCAAAAGCC GAAGTGCAGC TGGTGGAGTC TGG                               43

(2) INFORMATION FOR SEQ ID NO:23:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

TTACCCCTGT GGCAAAAGCC GAGGTGAAGC TGGTGGAATC TGG                               43

(2) INFORMATION FOR SEQ ID NO:24:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:24:

TTACCCCTGT GGCAAAAGCC CAGGTGCAGC TGAAGGAGTC AGG                               43

(2) INFORMATION FOR SEQ ID NO:25:
```

(i) SEQUENCE CHARACTERISTICS:
    (A) LENGTH: 43 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:25:

TTACCCCTGT GGCAAAAGCC CAGGTTACGC TGAAAGAGTC TGG          43

(2) INFORMATION FOR SEQ ID NO:26:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:26:

TTACCCCTGT GGCAAAAGCC GAGGTGAAGC TGGATGAGAC TGG          43

(2) INFORMATION FOR SEQ ID NO:27:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:27:

TTACCCCTGT GGCAAAAGCC GAGGTAAAGC TTCTCGAGTC TGG          43

(2) INFORMATION FOR SEQ ID NO:28:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:28:

TTACCCCTGT GGCAAAAGCC GAAATGAGAC TGGTGGAATC TGG          43

(2) INFORMATION FOR SEQ ID NO:29:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:29:

TTACCCCTGT GGCAAAAGCC GAAGTGAAGC TGGTGGAGTC TGA          43

(2) INFORMATION FOR SEQ ID NO:30:

(i) SEQUENCE CHARACTERISTICS:
        (A) LENGTH: 43 base pairs
        (B) TYPE: nucleic acid

```
        (C) STRANDEDNESS: single
        (D) TOPOLOGY: linear (ii) MOLECULE TYPE: cDNA (xi) SEQUENCE DESCRIPTION: SEQ ID NO:30:

TTACCCCTGT GGCAAAAGCC CAGGTTCAGC TGCAACAGTC TGA                43

(2) INFORMATION FOR SEQ ID NO:31:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:31:

TTACCCCTGT GGCAAAAGCC GAGATCCAGC TGCAGCAGTC TGG                43

(2) INFORMATION FOR SEQ ID NO:32:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:32:

TTACCCCTGT GGCAAAAGCC GAAGTGATGC TGGTGGAGTC TGG                43

(2) INFORMATION FOR SEQ ID NO:33:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:33:

TTACCCCTGT GGCAAAAGCC GAGGTGCAGC CTGTTGAGTC TGG                43

(2) INFORMATION FOR SEQ ID NO:34:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:34:

TTACCCCTGT GGCAAAAGCC GACGTGAAGC ATATGGAGTC TGG                43

(2) INFORMATION FOR SEQ ID NO:35:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA
```

(xi) SEQUENCE DESCRIPTION: SEQ ID NO:35:

TTACCCCTGT GGCAAAAGCC GAAGTGAAGC TTGAGGAGTC TGG          43

(2) INFORMATION FOR SEQ ID NO:36:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:36:

TTACCCCTGT GGCAAAAGCC GAGGTCCAGC TTCAGCAGTC AGG          43

(2) INFORMATION FOR SEQ ID NO:37:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:37:

TTACCCCTGT GGCAAAAGCC CAGGTCCAGC TGCAGCAGTC TAG          43

(2) INFORMATION FOR SEQ ID NO:38:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:38:

TTACCCCTGT GGCAAAAGCC CAGGTCCAGC TGCAGCAGTC TCG          43

(2) INFORMATION FOR SEQ ID NO:39:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:39:

TTACCCCTGT GGCAAAAGCC GAGGTTCAGC TGCAGCAGTC TGT          43

(2) INFORMATION FOR SEQ ID NO:40:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:40:

TTACCCCTGT GGCAAAAGCC CAGGTCCAAC TGCAGCAGCC TGG          43

(2) INFORMATION FOR SEQ ID NO:41:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:41:

TTACCCCTGT GGCAAAAGCC GAGGTTCAGC TGCAGCAGTC TGG         43

(2) INFORMATION FOR SEQ ID NO:42:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:42:

TTACCCCTGT GGCAAAAGCC GAGGTCCAGC TGCAACAATC TGG         43

(2) INFORMATION FOR SEQ ID NO:43:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:43:

TTACCCCTGT GGCAAAAGCC CAGGTCCACG TGAAGCAGTC TGG         43

(2) INFORMATION FOR SEQ ID NO:44:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:44:

TTACCCCTGT GGCAAAAGCC GATGTGCAGC TTCAGGAGTC GGG         43

(2) INFORMATION FOR SEQ ID NO:45:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:45:

TTACCCCTGT GGCAAAAGCC CAAGTTACTC TAAAAGAGTC TGG         43

(2) INFORMATION FOR SEQ ID NO:46:

```
    (i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:46:

TTACCCCTGT GGCAAAAGCC GAAGTGCAGC TGTTGGAGAC TGG              43

(2) INFORMATION FOR SEQ ID NO:47:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:47:

TTACCCCTGT GGCAAAAGCC CAGATCCAGT TGGTGCAATC TGG              43

(2) INFORMATION FOR SEQ ID NO:48:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:48:

TTACCCCTGT GGCAAAAGCC GATGTGAACT TGGAAGTGTC TGG              43

(2) INFORMATION FOR SEQ ID NO:49:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:49:

TTACCCCTGT GGCAAAAGCC CAGGCTTATC TACAGCAGTC TGG              43

(2) INFORMATION FOR SEQ ID NO:50:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:50:

TTACCCCTGT GGCAAAAGCC CAGGTCCAAG TGCAGCAGCC TGG              43

(2) INFORMATION FOR SEQ ID NO:51:

(i) SEQUENCE CHARACTERISTICS:
        (A) LENGTH: 43 base pairs
        (B) TYPE: nucleic acid
        (C) STRANDEDNESS: single
```

(D) TOPOLOGY: linear (ii) MOLECULE TYPE: cDNA (xi) SEQUENCE DESCRIPTION: SEQ ID NO:51:

TTACCCCTGT GGCAAAAGCC GAAGTGCAGC TGGTGGAGAC TGC          43

(2) INFORMATION FOR SEQ ID NO:52:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:52:

TTACCCCTGT GGCAAAAGCC GACGTGCAGG TGGTGGAGTC TGG          43

(2) INFORMATION FOR SEQ ID NO:53:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:53:

CTGCCCAACC AGCCATGGCC GATGTTTTGA TGACCCAAAC TCC          43

(2) INFORMATION FOR SEQ ID NO:54:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:54:

CTGCCCAACC AGCCATGGCC GACATCCAGA TGACCCAGTC TCC          43

(2) INFORMATION FOR SEQ ID NO:55:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:55:

CTGCCCAACC AGCCATGGCC GATATCCAGA TGACACAGAC TAC          43

(2) INFORMATION FOR SEQ ID NO:56:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:56:

CTGCCCAACC AGCCATGGCC GACATTGTGA TGACCCAGTC TCC                43

(2) INFORMATION FOR SEQ ID NO:57:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:57:

CTGCCCAACC AGCCATGGCC AACATTGTGC TGACCCAATC TCC                43

(2) INFORMATION FOR SEQ ID NO:58:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:58:

CTGCCCAACC AGCCATGGCC GATGTTGTGA TGACCCAAAC TCC                43

(2) INFORMATION FOR SEQ ID NO:59:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:59:

CTGCCCAACC AGCCATGGCC GAAATTGTGC TCACCCAGTC TCC                43

(2) INFORMATION FOR SEQ ID NO:60:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:60:

CTGCCCAACC AGCCATGGCC AGTATTGTGA TGACCCAGAC TCC                43

(2) INFORMATION FOR SEQ ID NO:61:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:61:

CTGCCCAACC AGCCATGGCC GATATTGTGC TAACTCAGTC TCC                43

(2) INFORMATION FOR SEQ ID NO:62:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:62:

CTGCCCAACC AGCCATGGCC CAAATTGTTC TCACCCAGTC TCC        43

(2) INFORMATION FOR SEQ ID NO:63:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:63:

CTGCCCAACC AGCCATGGCC GACATTCAGC TGACCCAGTC TCC        43

(2) INFORMATION FOR SEQ ID NO:64:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:64:

CTGCCCAACC AGCCATGGCC GATATTGTGA TGACCCAGGC TGC        43

(2) INFORMATION FOR SEQ ID NO:65:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:65:

CTGCCCAACC AGCCATGGCC GACCTTGTGC TGACACAGTC TCC        43

(2) INFORMATION FOR SEQ ID NO:66:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:66:

CTGCCCAACC AGCCATGGCC GAAAATGTGC TCACCCAGTC TCC        43

(2) INFORMATION FOR SEQ ID NO:67:

(i) SEQUENCE CHARACTERISTICS:

(A) LENGTH: 43 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:67:

CTGCCCAACC AGCCATGGCC GAAACAACTG TGACCCAGTC TCC          43

(2) INFORMATION FOR SEQ ID NO:68:

(i) SEQUENCE CHARACTERISTICS:
      (A) LENGTH: 43 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:68:

CTGCCCAACC AGCCATGGCC GATGCTGTGA TGACCCAGAT TCC          43

(2) INFORMATION FOR SEQ ID NO:69:

(i) SEQUENCE CHARACTERISTICS:
      (A) LENGTH: 43 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:69:

CTGCCCAACC AGCCATGGCC GACATCTTGC TGACTCAGTC TCC          43

(2) INFORMATION FOR SEQ ID NO:70:

(i) SEQUENCE CHARACTERISTICS:
      (A) LENGTH: 43 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:70:

CTGCCCAACC AGCCATGGCC GATGTTGTGA TAACTCAGGA TGA          43

(2) INFORMATION FOR SEQ ID NO:71:

(i) SEQUENCE CHARACTERISTICS:
      (A) LENGTH: 43 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:71:

CTGCCCAACC AGCCATGGCC GATGTTGTGG TGACTCAAAC TCC          43

(2) INFORMATION FOR SEQ ID NO:72:

(i) SEQUENCE CHARACTERISTICS:
      (A) LENGTH: 43 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:72:

CTGCCCAACC AGCCATGGCC AACATTGTGA TGGCCTGGTC TCC                              43

(2) INFORMATION FOR SEQ ID NO:73:

(i) SEQUENCE CHARACTERISTICS:
             (A) LENGTH: 43 base pairs
             (B) TYPE: nucleic acid
             (C) STRANDEDNESS: single
             (D) TOPOLOGY: linear (ii) MOLECULE TYPE: cDNA (xi) SEQUENCE DESCRIPTION: SEQ ID NO:73:

CTGCCCAACC AGCCATGGCC TCATTATTGC AGGTGCTTGT GGG                              43

(2) INFORMATION FOR SEQ ID NO:74:

(i) SEQUENCE CHARACTERISTICS:
             (A) LENGTH: 43 base pairs
             (B) TYPE: nucleic acid
             (C) STRANDEDNESS: single
             (D) TOPOLOGY: linear (ii) MOLECULE TYPE: cDNA (xi) SEQUENCE DESCRIPTION: SEQ ID NO:74:

CTGCCCAACC AGCCATGGCC GATATTGTGA TAACCCAGGA TGA                              43

(2) INFORMATION FOR SEQ ID NO:75:

(i) SEQUENCE CHARACTERISTICS:
             (A) LENGTH: 43 base pairs
             (B) TYPE: nucleic acid
             (C) STRANDEDNESS: single
             (D) TOPOLOGY: linear (ii) MOLECULE TYPE: cDNA (xi) SEQUENCE DESCRIPTION: SEQ ID NO:75:

CTGCCCAACC AGCCATGGCC GACATTGTGA TGACCCAGTC TCA                              43

(2) INFORMATION FOR SEQ ID NO:76:

(i) SEQUENCE CHARACTERISTICS:
             (A) LENGTH: 43 base pairs
             (B) TYPE: nucleic acid
             (C) STRANDEDNESS: single
             (D) TOPOLOGY: linear (ii) MOLECULE TYPE: cDNA (xi) SEQUENCE DESCRIPTION: SEQ ID NO:76:

CTGCCCAACC AGCCATGGCC GAAATGGTTC TCACCCAGTC TCC                              43

(2) INFORMATION FOR SEQ ID NO:77:

(i) SEQUENCE CHARACTERISTICS:
             (A) LENGTH: 43 base pairs
             (B) TYPE: nucleic acid
             (C) STRANDEDNESS: single
             (D) TOPOLOGY: linear (ii) MOLECULE TYPE: cDNA (xi) SEQUENCE DESCRIPTION: SEQ ID NO:77:

```
CTGCCCAACC AGCCATGGCC GATGTTGTGC TGACCCAAAC TCC                43
```

(2) INFORMATION FOR SEQ ID NO:78:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:78:

```
CTGCCCAACC AGCCATGGCC GACGTTGTGA TGTCACAGTC TCC                43
```

(2) INFORMATION FOR SEQ ID NO:79:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:79:

```
CTGCCCAACC AGCCATGGCC GACATTGTGA CGTCACAGTC TCC                43
```

(2) INFORMATION FOR SEQ ID NO:80:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:80:

```
CTGCCCAACC AGCCATGGCC CAAGTTGTTC TCACCCAGTC TCC                43
```

(2) INFORMATION FOR SEQ ID NO:81:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:81:

```
CTGCCCAACC AGCCATGGCC GACGTCCAGA TAACCCAGTC TCC                43
```

(2) INFORMATION FOR SEQ ID NO:82:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:82:

```
GATGGGGGTG TCGTTTTGGC                                          20
```

```
(2) INFORMATION FOR SEQ ID NO:83:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:83:

ACAGTTGGTG CAGCATCAGC                                              20

(2) INFORMATION FOR SEQ ID NO:84:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:84:

TATTTCCAGC TTGGTCCCTC TAGAGTTAAC GATATCAACG TTTATCTAAT CAGCAAGAGA   60

TGGAGGCTTG                                                         70

(2) INFORMATION FOR SEQ ID NO:85:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:85:

TGAGGTTCCT TGACCCCACT GCAGAGTACT AGGCCTCTGA GCTACTCAGT TAGGTGATTG   60

AGTAGCCAGT                                                         70
```